US012396807B2

United States Patent
Flexman et al.

(10) Patent No.: US 12,396,807 B2
(45) Date of Patent: Aug. 26, 2025

(54) OSS GUIDING AND MONITORING SYSTEMS, CONTROLLERS AND METHODS

(71) Applicant: KONINKLIJKE PHILIPS N.V., Eindhoven (NL)

(72) Inventors: Molly Lara Flexman, Melrose, MA (US); Paul Thienphrapa, Cambridge, MA (US); Torre Michelle Bydlon, Melrose, MA (US); Alexandru Patriciu, Belmont, MA (US); Ashish Panse, Burlington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1287 days.

(21) Appl. No.: 16/495,409

(22) PCT Filed: Mar. 19, 2018

(86) PCT No.: PCT/EP2018/056795
§ 371 (c)(1),
(2) Date: Sep. 19, 2019

(87) PCT Pub. No.: WO2018/172237
PCT Pub. Date: Sep. 27, 2018

(65) Prior Publication Data
US 2020/0022764 A1  Jan. 23, 2020

Related U.S. Application Data

(60) Provisional application No. 62/474,118, filed on Mar. 21, 2017.

(51) Int. Cl.
*A61B 34/30* (2016.01)
*A61B 5/06* (2006.01)
(Continued)

(52) U.S. Cl.
CPC .............. *A61B 34/30* (2016.02); *A61B 5/065* (2013.01); *A61B 34/20* (2016.02); *A61B 34/76* (2016.02);
(Continued)

(58) Field of Classification Search
CPC .................................................... A61B 5/065
See application file for complete search history.

(56) References Cited

U.S. PATENT DOCUMENTS

2008/0285909 A1* 11/2008 Younge ................ A61B 5/6852
385/13
2013/0204124 A1* 8/2013 Duindam ........... A61B 10/0233
604/272
(Continued)

FOREIGN PATENT DOCUMENTS

WO    2007111737    10/2007
WO    2014155303    10/2014
(Continued)

OTHER PUBLICATIONS

International Search Report and Written Opinion Dated Jul. 10, 2018 For International Application No. PCT/EP2018/056795 Filed Mar. 19, 2018.

*Primary Examiner* — Chad H Smith

(57) ABSTRACT

An OSS guiding and monitoring system employs an interventional device (40) including an integration of a OSS sensor (20) and one or more interventional tools (30), the OSS sensor (20) for generating shape sensing data informative of a shape of the OSS sensor (20) as the interventional device (40) is navigated within an anatomical region. The OSS guiding and monitoring system further employs an OSS guiding controller (90) for controlling a reconstruction of a shape of the interventional device (40) within the anatomical region responsive to a generation of the shape sensing data by the OSS sensor (20), and an OSS monitoring
(Continued)

controller (100) for controlling a monitoring of a degree of folding and/or a degree of twisting of the interventional device (40) within the anatomical region.

10 Claims, 19 Drawing Sheets

(51) Int. Cl.
    *A61B 34/00*     (2016.01)
    *A61B 34/20*     (2016.01)
    *B25J 19/02*     (2006.01)
    *G01D 5/353*     (2006.01)
    *G02B 6/02*     (2006.01)

(52) U.S. Cl.
    CPC ........... *B25J 19/021* (2013.01); *B25J 19/025* (2013.01); *G01D 5/353* (2013.01); *G02B 6/02076* (2013.01); *A61B 2034/2061* (2016.02)

(56) References Cited

U.S. PATENT DOCUMENTS

| | | |
|---|---|---|
| 2014/0276233 A1 | 9/2014 | Murphy |
| 2014/0276938 A1 | 9/2014 | Hsu |
| 2016/0008089 A1* | 1/2016 | Noonan .................. A61B 34/76 600/424 |
| 2017/0231699 A1 | 8/2017 | Flexman |

FOREIGN PATENT DOCUMENTS

| | | |
|---|---|---|
| WO | 2015049142 | 4/2015 |
| WO | 2016088037 | 6/2016 |
| WO | 2016/116821 | 7/2016 |
| WO | 2016/135966 | 9/2016 |
| WO | 2017055620 | 4/2017 |

* cited by examiner

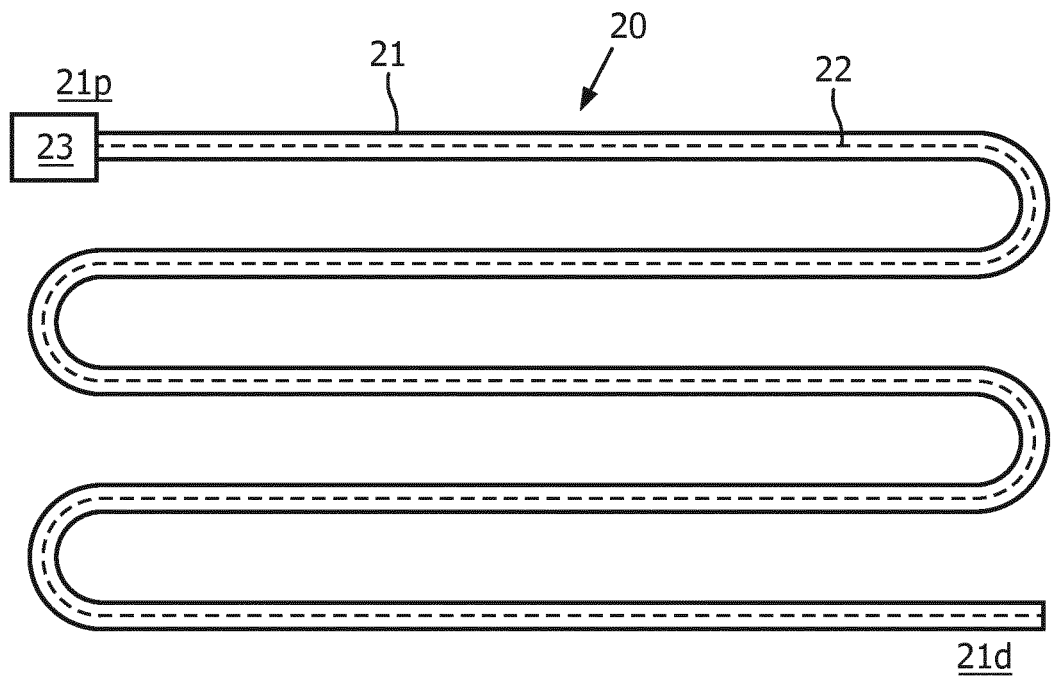
FIG. 1A
(prior art)
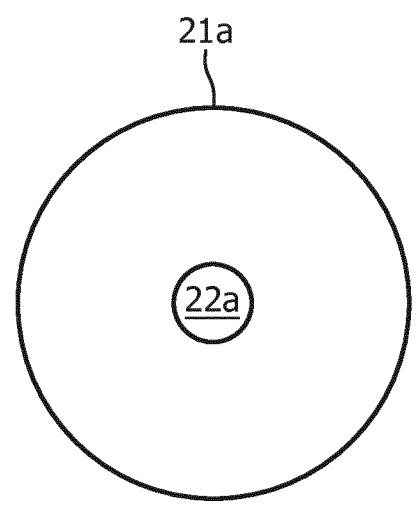 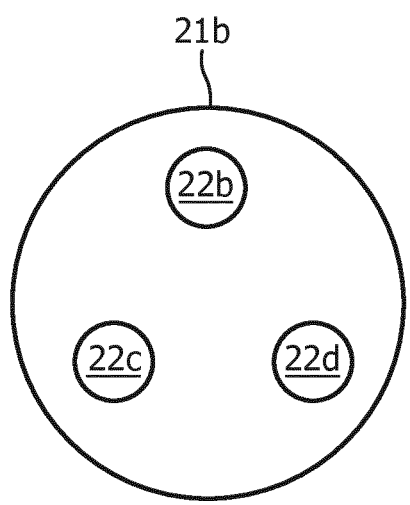
FIG. 1B
(prior art)
FIG. 1C
(prior art)

OSS GUIDING AND MONITORING SYSTEMS, CONTROLLERS AND METHODS

CROSS REFERENCE TO RELATED APPLICATIONS

This application is the U.S. National Phase application under 35 U.S.C. § 371 of International Application No. PCT/EP2018/056795 filed Mar. 19, 2018, published as WO 2018/172237 on Sep. 27, 2018, which claims the benefit of U.S. Provisional Patent Application No. 62/474,118 filed Mar. 21, 2017. These applications are hereby incorporated by reference herein.

FIELD OF THE INVENTION

The inventions of the present disclosure generally relate to systems, controllers and methods implementing optical shape sensing (OSS) technology for guiding a navigation of an interventional tool within an anatomical system of a patient (e.g., a tracking of linear/curvilinear translation(s) and/or an axial/non-axial rotation(s) of an OSS sensor integrated into a interventional tool be navigated within a cardiovascular system, a respiratory system or a digestive system of the patient).

The inventions of the present disclosure more particularly relate to improving such systems, controllers and methods by providing a monitoring of the optical shape sensing (OSS) guiding of the navigation of the interventional tool within the anatomical system of the patient (e.g., a monitoring of any folding and/or any twisting of a OSS sensor as an interventional tool is linearly/curvilinearly translated and/or axially/non-axially rotated within a lumen of a cardiovascular system, a respiratory system or a digestive system of the patient).

BACKGROUND OF THE INVENTION

Optical shape sensing (OSS) uses light along a single core or a multicore optical fiber for device localization and navigation during surgical intervention. The principle involved makes use of distributed strain measurements in the optical fiber using characteristic Rayleigh backscatter or controlled grating patterns. The shape along the optical fiber begins at a specific point along the sensor, known as the launch or z=0, and the subsequent shape position and orientation of the optical fiber are relative to that point.

An OSS fiber may be integrated into an interventional tool (e.g., vascular tools, endoluminal tools and orthopedic tools) to thereby provide live visual guiding via a monitor of the interventional tool during a minimally invasive procedure whereby the integrated OSS fiber provides a position (i.e., a location and/or an orientation) of a portion or an entirety of the interventional tool. While the live visual guiding of the interventional tool has proven advantageous for facilitating a successful minimally invasive procedure, issues of "pushability" and "torquability" of the interventional tool are a concern to potential "buckling" and a potential "whipping" of the interventional tool.

For example, a vascular navigation may be performed by passing a catheter over a guidewire whereby a mechanical interaction between the guidewire and the catheter primarily consists of (1) an advancement and/or a retraction of the guidewire and/or the catheter within the vasculature, and/or (2) a rotation of the guidewire and/or the catheter within the vasculature.

Ideally, the guidewire and the catheter have a 1-to-1 mapping between (1) an operator controlled translation and/or rotation of a proximal segment of the guidewire extraneous to the patient and/or a proximal segment of the catheter extraneous to the patient and (2) a corresponding translation and/or rotation of a distal segment of the guidewire and/or a distal segment of the catheter within the patient.

The guidewire and the catheter will have the aforementioned 1-to-1 mapping between the proximal segments and the distal segments when both segments of the guidewire and the catheter are straight and stiff. However, for a minimally invasive procedure, the distal segments of the guidewire and of the catheter must be sufficiently flexible to be navigated through a tortuous vasculature. Such flexibility may degrade the pushability and/or the torquability of the guidewire and/or the catheter.

More particularly, pushability relates to an achievable degree of a 1-1 mapping between the proximal segment(s) and the distal segment(s) of the guidewire and/or of the catheter as the extraneous proximal segment(s) are operator controlled or robotically controlled to advance or retract the distal segment(s) within the vasculature. A degrading of the pushability of the guidewire and/or of the catheter may result in a degree of folding of the distal segment(s) of the guidewire and/or of the catheter within the vasculature whereby the folding may negatively affect manipulation and guiding of the guidewire and/or of the catheter within the vasculature and/or may apply excessive stress within the vasculature.

Torquability relates to an achievable degree of a 1-1 mapping between the proximal segment(s) and the distal segment(s) of the guidewire and/or the catheter as the extraneous proximal segment(s) are operator controlled or robotically controlled to rotate the distal segment(s) within the vasculature. A degrading of the torquability of the guidewire and/or of the catheter may result in a degree of twisting of the distal segment(s) of the guidewire and/or of the catheter within the vasculature whereby the twisting may potentially and dangerously whip the guidewire and/or the catheter within the vasculature and/or may also apply excessive stress within the vasculature. Degraded torquability may also impede optimal manipulation and guidance of the guidewire and/or catheter.

Thus, there is a need to detect any potential buckling of an interventional tool within a patient, which is a delineated unacceptable degree of distortion of a navigated shape of the interventional tool within an anatomical region of the patient due to a folding of the interventional tool.

There is also a need to detect any potential whipping of an interventional tool within a patient, which is a delineated unacceptable degree of distortion of a navigated shape of the interventional tool within an anatomical region of the patient due to a twisting of the interventional tool.

SUMMARY OF THE INVENTION

To improve upon Optical Shape Sensing (OSS) guiding systems, controller and methods, the present disclosure provides inventions for a detection of any folding and/or any twisting of an interventional device including an integration of an interventional tool and an OSS sensor as the interventional device is navigated within an anatomical region by a linear/curvilinear translation of interventional device within the anatomical region and/or by an axial/non-axial rotation of the interventional device within the anatomical region.

For purposes of describing and claiming the inventions of the present disclosure:

(1) the term "anatomical region" broadly encompasses, as known in the art of the present disclosure and exemplary described in the present disclosure, one or more anatomical systems with each anatomical system having a natural or a surgical structural configuration for a navigation of an interventional device therein. Examples of an anatomical region include, but are not limited to, an integumentary system (e.g., skin and appendages), a skeletal system, a muscular system, a nervous system, an endocrine system (e.g., glands and pancreas), a digestive system (e.g., stomach, intestines, and colon), a respiratory system (e.g., airways and lungs), a circulatory system (e.g., heart and blood vessels), a lymphatic system (e.g., lymph nodes), a urinary system (e.g., kidneys), and reproductive system (e.g., uterus);

(2) the term "interventional tool" is to be broadly interpreted as known in the art of the present disclosure including interventional tools known prior to and conceived after the present disclosure. Examples of an interventional tool include, but are not limited to, vascular interventional tools (e.g., guidewires, catheters, stents sheaths, balloons, atherectomy catheters, IVUS imaging probes, deployment systems, etc.), endoluminal interventional tools (e.g., endoscopes, bronchoscopes, etc.) and orthopedic interventional tools (e.g., k-wires and screwdrivers);

(3) the term "tool node" broadly encompass a single point, multiple points, a segment, a template (e.g., shape, curvature or strain) or otherwise any portion of the interventional tool as known in the art of the present disclosure, and the labeling of a tool node as a "proximal tool node" or a "distal tool node" characterizes a relative longitudinal spacing of that particular tool node to another tool node of the interventional device and does not characterize an exact location of that particular tool node within the configuration of the interventional tool;

(4) the term "OSS sensor" broadly encompasses an optical fiber structurally configured, as known in the art of the present disclosure and hereinafter conceived, for extracting high density strain measurements of the optical fiber derived from light emitted into and propagated through the optical fiber and reflected back within the optical fiber in an opposite direction of the propagated light and/or transmitted from the optical fiber in a direction of the propagated light. An example of an OSS sensor includes, but is not limited to, an optical fiber structurally configured under the principle of Optical Frequency Domain Reflectometry (OFDR) for extracting high density strain measurements of the optical fiber derived from light emitted into and propagated through the optical fiber and reflected back within the optical fiber in an opposite direction of the propagated light and/or transmitted from the optical fiber in a direction of the propagated light via controlled grating patterns within the optical fiber (e.g., Fiber Bragg Grating), a characteristic backscatter of the optical fiber (e.g., Rayleigh backscatter) or any other arrangement of reflective node element(s) and/or transmissive node element(s) embedded, etched, imprinted, or otherwise formed in the optical fiber;

(5) the term "OSS node" broadly encompass any reflective node element or any transmissive node element of the OSS sensor as known in the art of the present disclosure, and the labeling of an OSS node as a "proximal OSS node" or a "distal OSS node" characterizes a relative longitudinal spacing of that particular OSS node to another OSS node as exemplary described in the present disclosure and does not characterize an exact location of that particular OSS node within the structural configuration of the OSS sensor;

(6) the phrase "integration of an interventional tool and an OSS sensor" broadly encompasses any type of combining, adjoining, attaching, mounting, insertion, intermingling or otherwise integrating of an interventional tool and an OSS sensor into an interventional device as understood in the art of the present disclosure and exemplary described. Examples of such an integration include, but are not limited to, a fixed insertion of an OSS sensor within a channel of a catheter and a guidewire incorporating an OSS sensor;

(7) the term "device node" broadly encompass a single point, multiple points, a segment, a template (e.g., shape, curvature or strain) or otherwise any portion of the interventional device as known in the art of the present disclosure, and the labeling of a device node as a "proximal device node" or a "distal device node" characterizes a relative longitudinal spacing of that particular device node to another device node of the interventional device and does not characterize an exact location of that particular device node within the configuration of the interventional device. Examples of a device node include, but are not limited to, an OSS node of the OSS sensor and a tool node of the interventional tool mapped to an OSS node of the OSS sensor.

(8) the phrase "folding of the interventional device" broadly encompasses any decrease in a longitudinal spacing between a proximal device node of the interventional device extraneous to the anatomical region and a distal device node of the interventional device within the anatomical region as understood in the art of the present disclosure and as exemplary descried herein; and (9) the phrase "twisting of the interventional device" broadly encompasses any increase in an angular orientation between a proximal device node of the interventional device extraneous to the anatomical region and a distal device node of an OSS sensor within the anatomical region as understood in the art of the present disclosure and as exemplary descried herein.

One embodiment of the inventions of the present disclosure is an OSS guiding and monitoring system employing an interventional device including an integration of a FOR sensor and one or more interventional tools. The OSS guiding and monitoring system further employs an OSS guiding and monitoring device including an OSS guiding controller and an OSS monitoring controller.

In operation, the OSS sensor generates shape sensing data informative of a shape of the OSS sensor as the interventional device is navigated within an anatomical region (e.g., translated and/or rotated within the anatomical region).

The OSS guiding controller controls a reconstruction of a shape of the interventional device within the anatomical region responsive to a generation of the shape sensing data by the OSS sensor.

The OSS monitoring controller controls a monitoring of a degree of folding and/or a degree of twisting of the interventional device within the anatomical region by generating a pushability metric and/or a torquability metric responsive to a generation of the shape sensing data by the OSS sensor.

The pushability metric quantifies an estimated degree of folding of the interventional device between a proximal device node and a distal device node of the interventional device.

The torquability metric quantifies an estimated degree of twisting of the interventional device between the proximal device node and the distal device node of the interventional device.

A second embodiment of the inventions of the present disclosure is the OSS guiding and monitoring device including the OSS guiding controller and the OSS monitoring controller.

A third embodiment of the inventions of the present disclosure is OSS guiding and monitoring method for the interventional device including the integration of the OSS sensor and the interventional tool(s).

The OSS guiding and monitoring method involves the OSS sensor generating shape sensing data informative of a shape of the OSS sensor as the interventional device is navigated within an anatomical region (e.g., translated and/or rotated within the anatomical region).

The OSS guiding and monitoring method further involves the OSS guiding controller controlling a reconstruction of a shape of the interventional device within the anatomical region responsive to a generation of the shape sensing data by the OSS sensor.

The OSS guiding and monitoring method further involves the OSS monitoring controller controlling a monitoring of a folding and/or a twisting of the interventional device within the anatomical region by generating the pushability metric and/or the torquability metric responsive to a generation of the shape sensing data by the OSS sensor.

For all embodiments of the inventions of the present disclosure, the OSS monitoring controller may derive the pushability metric via the shape sensing data on a temporal frame basis by detecting:
1. an advancement of a proximal device node of the interventional device extraneous to the anatomical region without a corresponding advancement of a distal device node of the interventional device within the anatomical region;
2. a region of a longitudinal curvature change of the interventional device between a proximal device node and a distal device node of the interventional device as the interventional device is navigated within the anatomical region;
3. excessive forces on the interventional device as the interventional device is navigated within the anatomical region; and
4. excessive transverse motion by the interventional device as the interventional device is navigated within the anatomical region.

For buckling warning purposes, the OSS monitoring controller may ascertain a potential for a buckling of the interventional device responsive to the pushability metric having a non-zero magnitude exceeding a folding (non-buckling threshold) delineating a folding of the interventional device whereby the interventional tool is capable of being further advanced within the anatomical region, and/or the pushability metric having a non-zero magnitude exceeding a buckling threshold delineating a folding of the interventional device whereby the interventional tool is incapable of being further advanced within the anatomical region.

A folding warning and/or a buckling warning may be communicated by the OSS monitoring controller by:

1. a textual display warning (e.g., a textual folding/buckling message overlaying a displayed shape reconstruction of the interventional device),
2. an auditory warning (e.g., an auditory message verbalizing a folding or a buckling of the interventional device);
3. a visual display warning (e.g., a color encoded folding/buckling warning of a displayed shape reconstruction of the interventional device);
4. a visual device warning (e.g., an energizing of a hub LED of the interventional device), and
5. a haptic warning (e.g., a vibration of a hub motor of interventional device).

Further for all embodiments of the inventions of the present disclosure, the OSS monitoring controller may derive the torquability metric via the shape sensing data on a temporal frame basis by detecting:
1. a rotation of a proximal device node of the interventional device extraneous to the anatomical region without a corresponding rotation of a distal device node of the interventional device within the anatomical region; and
2. a region of an axial rotation of the interventional device between the proximal device node and the distal device node of the interventional device as the interventional device is navigated within the anatomical region.

For whipping warning purposes, the OSS monitoring controller may ascertain a potential for a whipping of the interventional device responsive to the torquability metric having a non-zero magnitude exceeding a twisting (non-whipping) threshold delineating a twisting of the interventional device insusceptible to a whipping of the interventional device within the anatomical region, and/or the torquability metric having a non-zero magnitude exceeding a whipping threshold indicative of a delineated twisting of the interventional device susceptible to a whipping of the interventional device within the anatomical region.

A twisting warning and/or whipping warning may be communicated by the OSS monitoring controller by:
1. a textual display warning (e.g., a textual twisting/whipping message overlaying a displayed shape reconstruction of the interventional device),
2. an auditory warning (e.g., an auditory message verbalizing a twisting or a whipping of the interventional device);
3. a visual display warning (e.g., a color encoded twisting/warning of a displayed shape reconstruction of the interventional device);
4. a visual device warning (e.g., an energizing of a hub LED of the interventional device), and
5. a haptic warning (e.g., a vibration of a hub motor of interventional device).

Also, for purposes of describing and claiming the inventions of the present disclosure:
(1) the term "OSS guiding and monitoring system" broadly encompasses all optical shape sensing based guiding systems utilized in interventional procedures for navigating an interventional device within an anatomical region, as known in the art of the present disclosure and hereinafter conceived, incorporating the inventive principles of the present disclosure for monitoring a folding and/or a twisting of an interventional device within the anatomical region;
(2) the term "OSS guiding and monitoring method" broadly encompasses all optical shape sensing based guiding systems utilized in interventional procedures for navigating an interventional device within an anatomical region, as known in the art of the present disclosure and hereinafter conceived, incorporating the inventive principles of the present disclosure for monitoring a folding and/or a twisting of the interventional device within the anatomical region;

(3) the term "controller" broadly encompasses all structural configurations of an application specific main board or an application specific integrated circuit for controlling an application of various inventive principles of the present disclosure related to monitoring a folding and/or a twisting of an interventional device within an anatomical region as subsequently exemplarily described in the present disclosure. The structural configuration of the controller may include, but is not limited to, processor(s), computer-usable/computer readable storage medium(s), an operating system, application module(s), peripheral device controller(s), interface(s), bus(es), slot(s) and port(s). The labels "OSS guiding" and "OSS monitoring" used herein for the term "controller" distinguishes for identification purposes a particular controller from other controllers as described and claimed herein without specifying or implying any additional limitation to the term "controller".

(4) the term "application module" broadly encompasses a component of a controller consisting of an electronic circuit and/or an executable program (e.g., executable software and/or firmware stored on a non-transitory computer readable medium(s)) for executing a specific application. The labels "Shape Reconstruction", "Pushability Metric" and "Torquability Metric" used herein for the term "module" distinguishes for identification purposes a particular module from other modules as described and claimed herein without specifying or implying any additional limitation to the term "application module"; and (5) the terms "signal", "data", and "command" broadly encompasses all forms of a detectable physical quantity or impulse (e.g., voltage, current, or magnetic field strength) as understood in the art of the present disclosure and as exemplary described in the present disclosure for communicating information and/or instructions in support of applying various inventive principles of the present disclosure as subsequently described in the present disclosure. Signal/data/command communication between components of the present disclosure may involve any communication method, as known in the art of the present disclosure and hereinafter conceived, including, but not limited to, signal/data/command transmission/reception over any type of wired or wireless medium/datalink and a reading of signal/data/command uploaded to a computer-usable/computer readable storage medium.

The foregoing embodiments and other embodiments of the inventions of the present disclosure as well as various features and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of the present disclosure being defined by the appended claims and equivalents thereof.

BRIEF DESCRIPTION OF THE DRAWINGS

FIGS. 1A-1C illustrates exemplary embodiments of an OSS sensor as known in the art of the present disclosure.

DETAILED DESCRIPTION OF THE PREFERRED EMBODIMENTS

Figure 2:
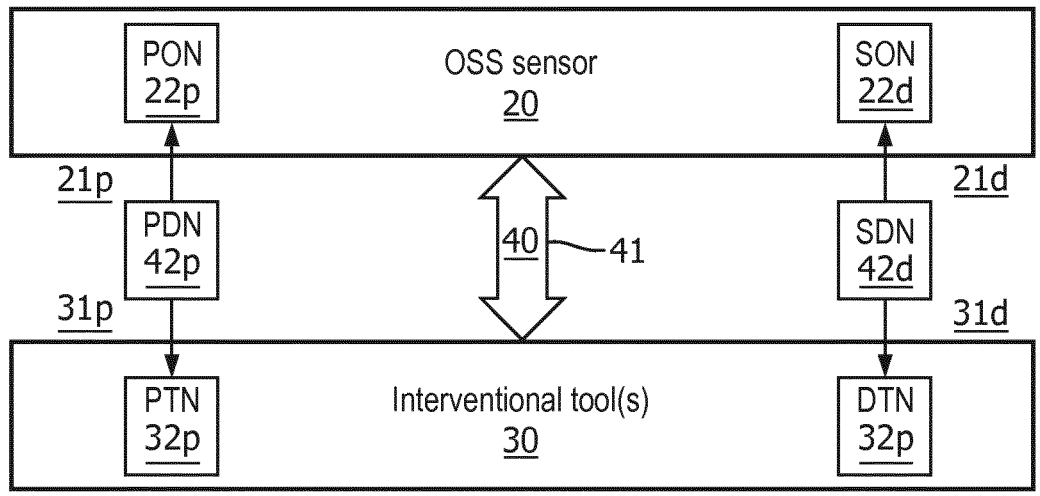
FIG. 2 illustrates an exemplary embodiment of an interventional device as known in the art of the present disclosure.

As an improvement upon prior optical shape sensing (OSS) based guiding systems, methods and controllers, the inventions of the present provide for a detection of any folding and/or any twisting of an interventional device including an integration of an interventional tool and a OSS sensor as the interventional device is navigated within an anatomical region by a linear/curvilinear translation of the interventional device within the anatomical region and/or by an axial/non-axial rotation of the interventional device within the anatomical region.

To facilitate an understanding of the various inventions of the present disclosure, the following description of FIGS. 1A-3B teaches an interventional device having an integration of an interventional tool and an OSS sensor as known in the art of the present disclosure. From this description, those having ordinary skill in the art will appreciate various and numerous embodiments of an interventional device applicable to an OSS guiding and monitoring of a navigation of the interventional device within an anatomical region in accordance with the inventive principles of the present disclosure. Please note the components of the present disclosure as shown in FIGS. 1A-3B are not drawn to scale, but drawn to conceptually support the inventive principles of the present disclosure.

Referring to FIG. 1A, an OSS sensor 20 applicable to the inventions of the present disclosure includes an optical fiber 21 as a single core optical fiber (e.g., an optical fiber 21a having a single core as shown in FIG. 1B) or a multi-core optical fiber (e.g. a multi-core optical fiber 21b having multi-cores 22b-22d as shown in FIG. 1C). A core of optical fiber 21 has controlled grating patterns (e.g., Fiber Bragg Gratings), a characteristic backscatter (e.g., Rayleigh backscatter) or any other arrangement of reflective elements and/or transmissive elements embedded, etched, imprinted, or otherwise formed in optical fiber 21. In practice, OSS nodes in the form of controlled gratings, characteristic backscatter, or reflective/transmissive elements may extend along any segment or an entirety of optical fiber 21 as symbolically shown by dashed line 22 extending from a proximal end 21p to a distal end 21d. Also, in practice, OSS sensor 20 may include two (2) or more individual optical fibers 21 that may or may not be helixed.

In practice, optical fiber 21 of OSS sensor 20 may be made partially or entirely of any glass, silica, phosphate glass or other glasses, or made of glass and plastic or plastic, or other materials used for making optical fibers. For impeding any damage to OSS sensor 20 when introduced into a patient anatomy via manual or robotic insertion, an optical fiber 21 of OSS sensor 20 may permanently encircled by a protective sleeve as known in the art.

In practice, the protective sleeve may be made from any flexible material of a specified hardness including, but not limited to, pebax, nitinol, furcation tubing, and stranded metal tubing. Also in practice, the protective sleeve may consist of two or more tubular components of same or different degrees of flexibility and hardness in an overlapping and/or sequential arrangement.

OSS sensor 20 may further include an optical connector 23 for connecting optical fiber 21 to another optical fiber, a launch or an optical source (e.g., optical integrator) as will be further described in the present disclosure.

Referring to FIG. 2, the inventions of the present disclosure are premised on an integration of a OSS sensor 20 and one or more interventional tools 30 to configure an interventional device 40 for an execution of an interventional procedure involving a navigation of interventional device 40 within one or more anatomical regions (e.g., a heart and blood vessels of cardiovascular system, airways and lungs of a respiratory system, a stomach and intestines of a digestive system, and bores within of a musculoskeletal system).

Examples of interventional tool 30 include, but are not limited to, vascular interventional tools (e.g., guidewires, catheters, stents sheaths, balloons, atherectomy catheters, IVUS imaging probes, deployment systems, etc.), endoluminal interventional tools (e.g., endoscopes, bronchoscopes, etc.) and orthopedic interventional tools (e.g., k-wires and screwdrivers).

In practice, an integration of OSS sensor 20 and interventional tool 30 may be in any configuration suitable for a particular interventional procedure.

Further in practice, a proximal device node 42p of interventional device 40 may be a proximal OSS node 22p of OSS sensor 20. Alternatively, proximal device node 42p of interventional device 40 may be a proximal tool node 32p mapped to proximal OSS node 22p of OSS sensor 20 via a mechanical relationship mapping or a shape template based mapping between proximal OSS node 22p and proximal tool node 32p as known in the art of the present disclosure.

Similarly in practice, a distal device node 42d of interventional device 40 may be a distal OSS node 22d of OSS sensor 20. Alternatively, distal device node 42d of interventional device 40 may be a distal tool node 32d mapped to distal OSS node 22d of OSS sensor 20 via a mechanical relationship mapping or a shape template based mapping between distal OSS node 22d and distal tool node 32d as known in the art of the present disclosure.

Figure 3A:
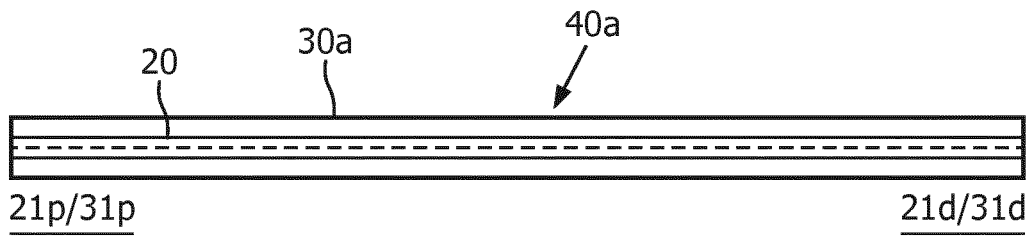
FIGS. 3A and 3B illustrate exemplary embodiments of an integration of an OSS sensor into a guidewire as known in the art of the present disclosure.
Figure 3B:
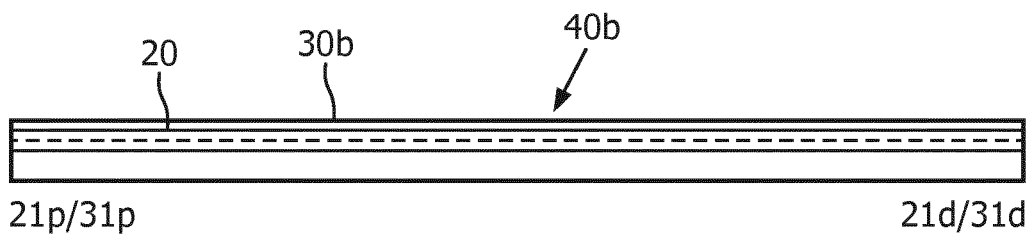

For example, FIG. 3A illustrates an OSS sensor 20 axially embedded within a guidewire 30a to configure an interventional device 40 in the form of an OSS guidewire 40a as known in the art of the present disclosure, and FIG. 3B illustrates OSS sensor 20 non-axially embedded within a guidewire 30b to configure an interventional device 40 in the form of an OSS guidewire 40b as known in the art of the present disclosure. OSS guidewire 40a and OSS guidewire 40b may be incorporated into any interventional procedure involving the utilization of a guidewire whereby the OSS guidewire 40a and OSS guidewire 40b may be navigated as necessary within anatomical region via a shape reconstruction capabilities of OSS sensor 20 as known in the art of the present disclosure.

Figure 4A:
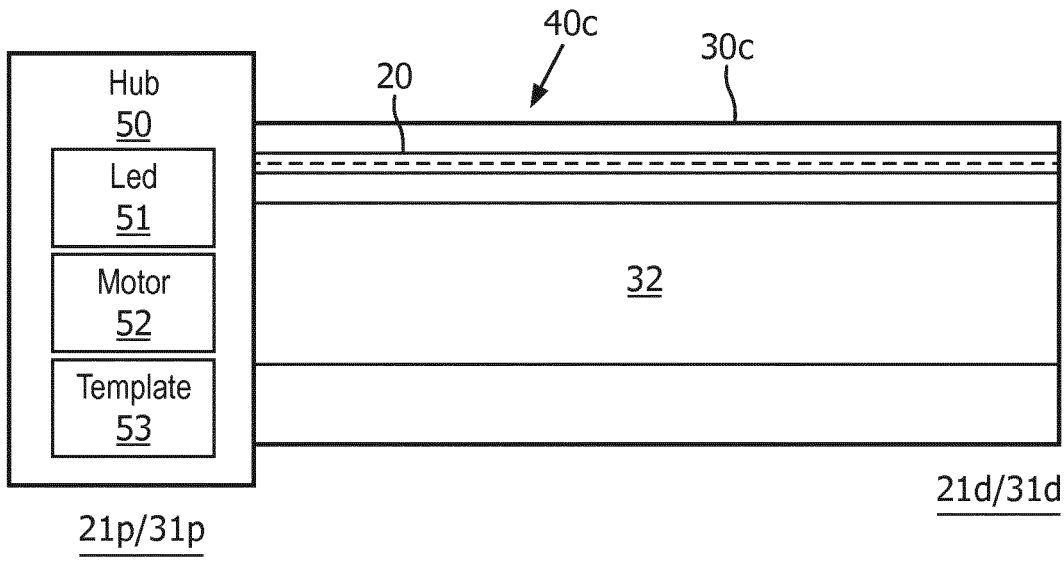
FIGS. 4A and 4B illustrate exemplary embodiments of an integration of an OSS sensor into catheter as known in the art of the present disclosure.
Figure 4B:
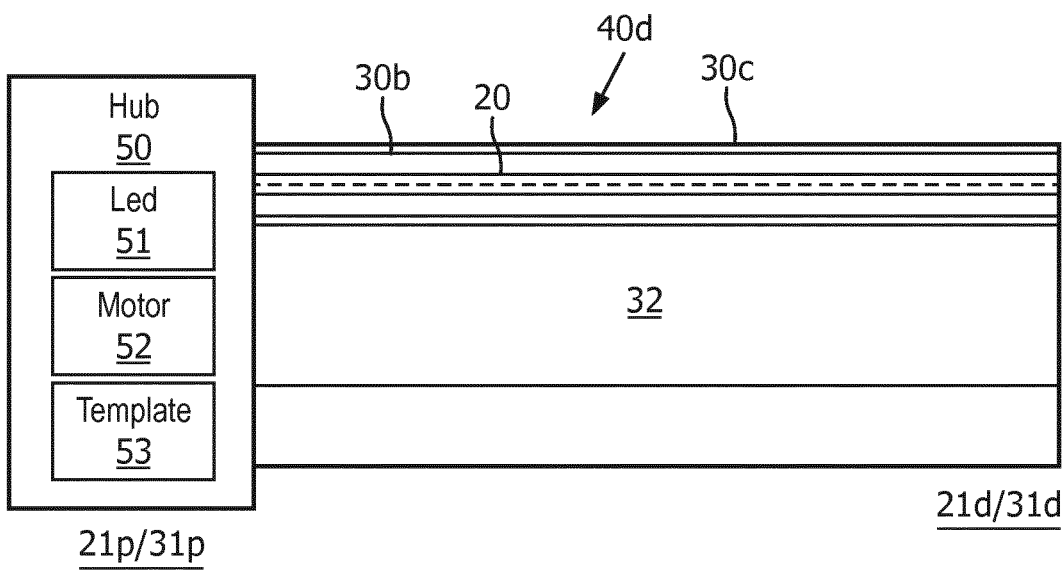

By further example, FIG. 4A illustrates a OSS sensor 20 temporarily or permanently inserted within a channel of a catheter 30c to configure an interventional device 40 in the form of a universal catheter 40c as known in the art of the present disclosure, and FIG. 4B illustrates an OSS guidewire 40b (FIG. 3B) temporarily or permanently inserted within a channel of catheter 30c to configure an interventional device 40 in the form of a universal catheter 40d as known in the art of the present disclosure. Universal catheter 40c and universal catheter 40d may be incorporated into any interventional procedure involving the utilization of a working channel 31c of catheter 30c whereby universal catheter 40c and universal catheter 40d may be navigated as necessary within anatomical region(s) via a shape reconstruction capabilities of OSS sensor 20 as known in the art of the present disclosure.

Still referring to FIGS. 4A and 4B, universal catheter 40c and universal catheter 40d may further employ a hub 50 for facilitating a navigation of universal catheter 40c and universal catheter 40d within anatomical regions as known in the art of the present disclosure. As will be further described in the present disclosure, in practice, hub 50 may include a light emitting diode 51 for providing visual feedback of an OSS monitoring of an interventional device attached to hub 50 in accordance with the inventive principles of the present disclosure, a vibrating motor 52 for providing haptic feedback of the OSS monitoring of an interventional device attached to hub 50 in accordance with the inventive principles of the present disclosure and/or an orientation template 53 for facilitating a generation of a torquability metric of an interventional device attached to hub 50 in accordance with the inventive principles of the present disclosure.

Referring back to FIG. 2, while proximal OSS node 22$p$ is shown as being located within a proximal end 21$p$ of OSS sensor 20 and distal OSS node 22$d$ is shown as being located within a distal end 21$d$ of OSS sensor 20, in practice proximal OSS node 22$p$ and distal OSS node 22$d$ may be located anywhere within the configuration of OSS sensor 20 limited only by a location of proximal OSS node 22$p$ being closer to proximal end 21$p$ of OSS sensor 20 than a location of distal OSS node 22$d$.

Similarly, while proximal tool node 32$p$ is shown as being located within a proximal end 31$p$ of interventional tool 30 and distal tool node 32$d$ is shown as being located within a distal end 31$d$ of interventional tool 30, in practice proximal tool node 32$p$ and distal tool node 32$d$ may be located anywhere within the configuration of interventional tool 30 limited only by a location of proximal tool node 32$p$ being closer to proximal end 31$p$ of interventional tool 30 than a location of distal tool node 32$d$.

More particularly, referring to FIGS. 3A and 3B, both OSS guidewire 40$a$ and OSS guidewire 40$b$ have a proximal device node (not shown) (e.g., proximal device node 41$p$ of FIG. 2) and a distal device node (not shown) (e.g., a distal device node 41 of FIG. 2) located between a proximal end 21$p$/31$p$ and a distal end 21$d$/31$d$ as designated for a particular interventional procedure. For example, a proximal device node may be located at or adjacent a proximal origin of OSS guidewire 40$a$ and a distal device node at or adjacent a distal tip of OSS guidewire 40$a$. Similarly, a proximal device node may be located at or adjacent a proximal origin of OSS guidewire 40$b$ and a distal device node at or adjacent a distal tip of OSS guidewire 40$b$.

Further, referring to FIGS. 4A and 4B, both universal catheter 40$c$ and universal catheter 40$d$ have a proximal device node (not shown) (e.g., proximal device node 41$p$ of FIG. 2) and a distal device node (not shown) (e.g., a distal device node 41 of FIG. 2) located between a proximal end 21$p$/31$p$ and a distal end 21$d$/31$d$ as designated for a particular interventional procedure. For example, a proximal device node may be located at or adjacent hub 50 of universal catheter 40$c$ and a distal device node at or adjacent a distal tip of universal catheter 40$c$. Similarly, a proximal device node may be located at hub 50 of universal catheter 40$d$ and a distal device node at or adjacent a distal tip of universal catheter 40$d$.

To facilitate a further understanding of the inventions of the present disclosure, the following description of FIGS. 5A-9B teaches a folding and a twisting of interventional device 40 (FIG. 2) within an anatomical lumen AL as known in the art of the present disclosure in support of a subsequent teaching of a monitoring of such folding and twisting of interventional device 40 within the anatomical lumen AL via a respective pushability metric and a torquability metric in accordance with the inventive principles of the present disclosure. While the illustration of FIGS. 5A-9B is of a folding and a twisting of a relatively short interventional device 40 within a straight anatomical lumen AL for purposes of simplifying the discussion herein of a folding and a twisting of interventional device 40 within anatomical lumen AL, those having ordinary skill in the art will appreciate in practice a highly elongated interventional device 40 will be navigated through a tortuous anatomical lumen AL, which increases the potential for a folding and/or a twisting of interventional device 40 within anatomical lumen AL.

From this description of FIGS. 5A-9B, those having ordinary skill in the art will appreciate the vast potential for a folding and/or a twisting of interventional device 40 within any anatomical region.

Please note the components of the present disclosure as shown in FIGS. 5A-9B are not drawn to scale, but drawn to conceptually support the inventive principles of the present disclosure.

Figure 5A:
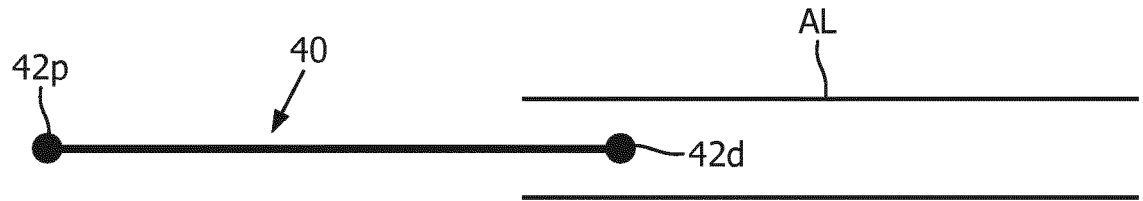
FIGS. 5A-5C illustrate an exemplary non-folding of an OSS sensor translated within an anatomical lumen as known in the art of the present disclosure.
Figure 5B:
Figure 5C:
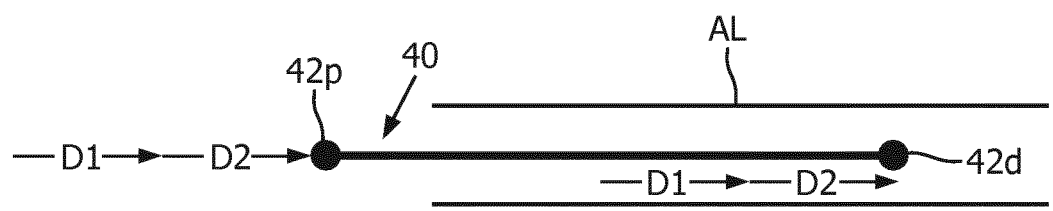

As to the drawings, FIGS. 5A-5C illustrate an exemplary navigation of interventional device 40 through anatomical lumen AL over a distance D1 and a distance D2 that does not involve any folding nor any twisting of interventional device 40 between proximal device node 42$p$ and distal device node 42$d$ as a proximal segment of interventional device 40 is advanced extraneous to anatomical lumen AL. In accordance with the inventive principles of the present disclosure, a pushability metric would provide an indication of a non-folding of interventional device 40 between proximal device node 42$p$ and distal device node 42$d$, and a torquability metric would provide an indication of a non-twisting of interventional device 40 between proximal device node 42$p$ and distal device node 42$d$.

Figure 6A:
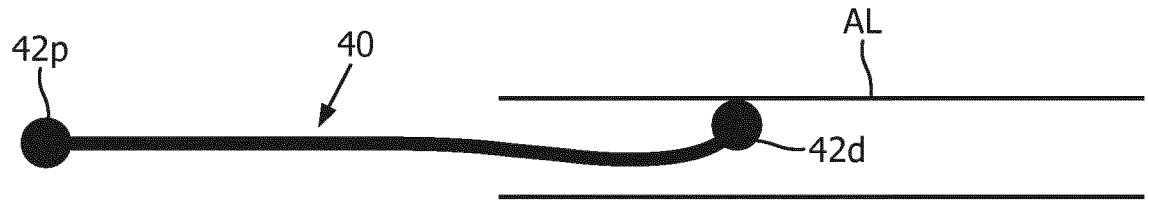
FIGS. 6A-6C illustrate a first exemplary folding and buckling of an OSS sensor translated within an anatomical lumen as known in the art of the present disclosure.
Figure 6B:
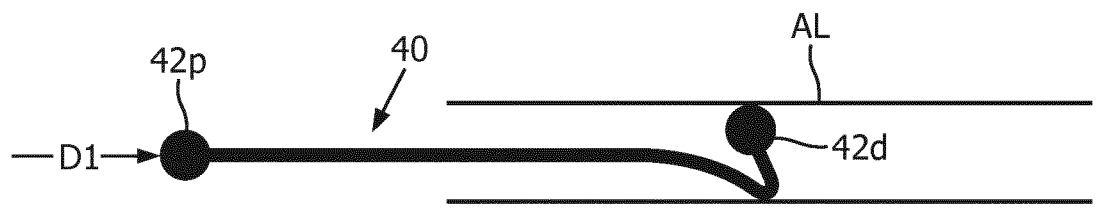
Figure 6C:
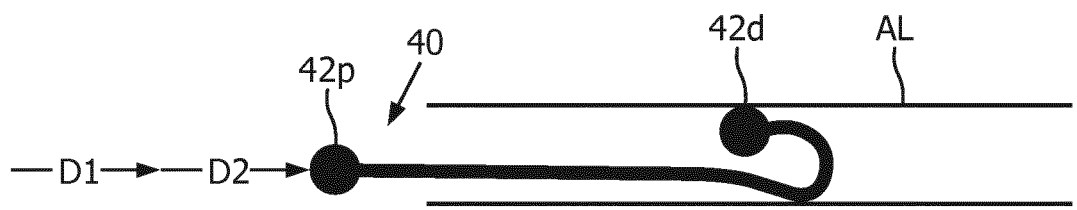

FIGS. 6A-6C illustrate an exemplary folding, non-twisting navigation of interventional device 40 through anatomical lumen AL over a distance D1 and a distance D2 that involves a folding of interventional device 40 between proximal device node 42$p$ and distal device node 42$d$ as a proximal segment of interventional device 40 is advanced extraneous to anatomical lumen AL. In accordance with the inventive principles of the present disclosure, a pushability metric would provide an indication of a folding/buckling of interventional device 40 between proximal device node 42$p$ and distal device node 42$d$, and a torquability metric would provide an indication of a non-twisting of interventional device 40 between proximal device node 42$p$ and distal device node 42$d$.

In accordance with the inventive principles of the present disclosure, a folding (non-buckling) threshold may be applied to the pushability metric whereby a warning of a folding of interventional device 40 within anatomical lumen AL may be communicated to an operator or a robot navigating interventional device 40 through anatomical lumen AL if the pushability metric exceeds the folding threshold, thereby warning the operator or the robot of a potential buckling of interventional device 40 within anatomical lumen AL (e.g., the interventional tool folding of FIG. 6B). From the folding warning, the operator or the robot may therefore retract the interventional device 40 within anatomical lumen AL to a degree that unfolds interventional device 40 within anatomical lumen AL.

Alternatively or concurrently, a buckling threshold may be applied to the pushability metric whereby a warning of a buckling of interventional device 40 within anatomical lumen AL may be communicated to an operator or a robot navigating interventional device 40 through anatomical lumen AL if the pushability metric exceeds the buckling threshold (e.g., the interventional tool buckling of FIG. 6C). From the buckling warning, the operator or the robot may understand a retraction of the interventional device 40 within anatomical lumen AL is imperative to thereby undo the buckling of interventional device 40 within anatomical lumen AL or to replace interventional device 40.

Figure 7A:
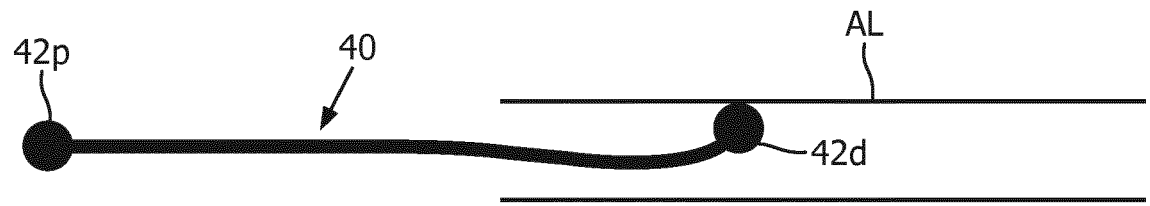
FIGS. 7A-7C illustrate a second exemplary folding and buckling of an OSS sensor translated within an anatomical lumen as known in the art of the present disclosure.
Figure 7B:
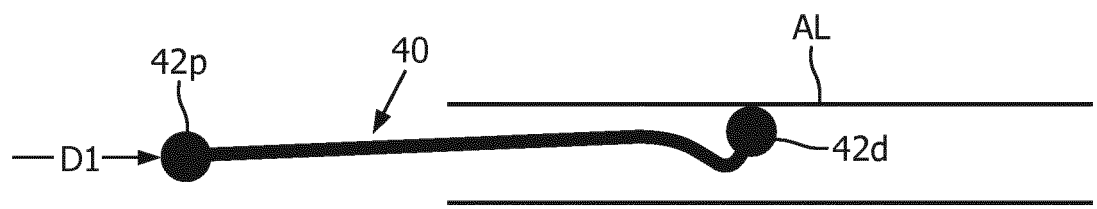
Figure 7C:
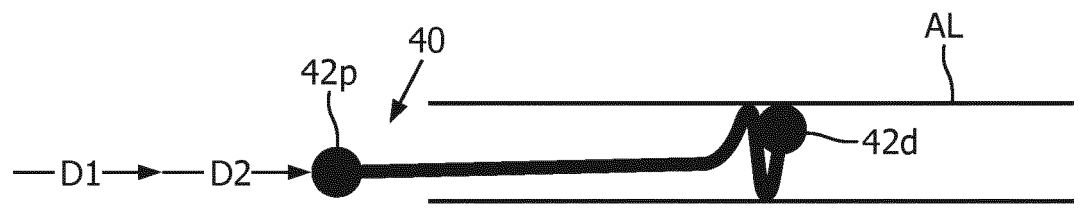

FIGS. 7A-7C illustrate another exemplary folding, non-twisting navigation of interventional device 40 through anatomical lumen AL over distance D1 and distance D2 that involves a folding of interventional device 40 between proximal device node 42*p* and distal device node 42*d* as a proximal segment of interventional device 40 is advanced extraneous to anatomical lumen AL. In accordance with the inventive principles of the present disclosure, a pushability metric would provide an indication of a folding or a buckling of interventional device 40 between proximal device node 42*p* and distal device node 42*d*, and a torquability metric would provide an indication of a non-twisting of interventional device 40 between proximal device node 42*p* and distal device node 42*d*. In response to the folding warning, the operator or the robot may retract interventional device 40 from anatomical lumen AL to a degree that nullifies the folding warning.

Again, in accordance with the inventive principles of the present disclosure, a folding (non-buckling) threshold may be applied to the pushability metric whereby a warning of a folding of interventional device 40 within anatomical lumen AL may be communicated to an operator or a robot navigating interventional device 40 through anatomical lumen AL if the pushability metric exceeds the folding threshold, thereby warn the operator or the robot of a potential buckling of interventional device 40 within anatomical lumen AL (e.g., the interventional tool folding of FIG. 7B). From the folding warning, the operator or the robot may therefore retract the interventional device 40 within anatomical lumen AL to a degree that unfolds interventional device 40 within anatomical lumen AL.

Alternatively or concurrently, a buckling threshold may be applied to the pushability metric whereby a warning of a buckling of interventional device 40 within anatomical lumen AL may be communicated to an operator or a robot navigating interventional device 40 through anatomical lumen AL if the pushability metric exceeds the buckling threshold (e.g., the interventional tool buckling of FIG. 7C). From the buckling warning, the operator or the robot may understand a retraction of the interventional device 40 within anatomical lumen AL is imperative to thereby undo the buckling of interventional device 40 within anatomical lumen AL or to replace interventional device 40.

Figure 8A:
FIGS. 8A-8C illustrate a first exemplary twisting and whipping of an OSS sensor translated within an anatomical lumen as known in the art of the present disclosure.

FIG. 8A illustrates an exemplary non-twisting rotation of interventional device 40 within anatomical lumen AL involving a synchronized rotation of proximal device node 42*p* and distal device node 42*d*.

Figure 8B:
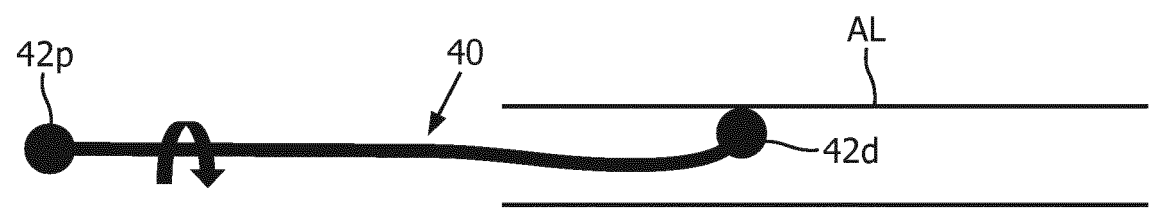
Figure 8C:
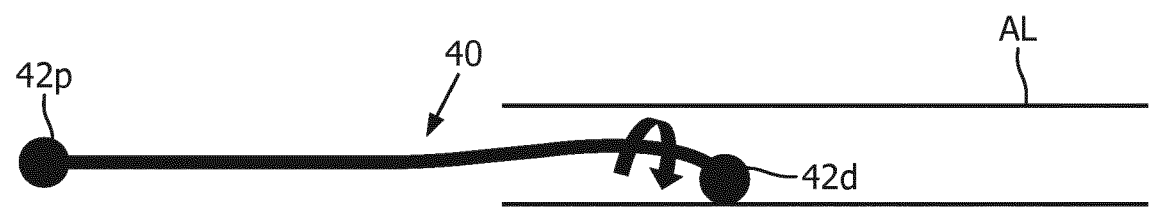

FIGS. 8B and 8C illustrate an exemplary non-folding, twisting rotation of interventional device 40 within anatomical lumen AL that involves a twisting of interventional device 40 between proximal device node 42*p* and distal device node 42*d* as a proximal segment of interventional device 40 is rotated extraneous to anatomical lumen AL. More particularly, FIG. 8B shows a rotation of proximal device node 42*p* extraneous to anatomical lumen AL and a non-rotation (or minimal) rotation of distal device node 42*d* within anatomical lumen AL that eventually results in a whipping of distal device node 42*d* within anatomical lumen AL as shown in FIG. 8C. In accordance with the inventive principles of the present disclosure, a pushability metric would provide an indication of a non-folding of interventional device 40 between proximal device node 42*p* and distal device node 42*d*, and a torquability metric would provide an indication of a twisting or a whipping of interventional device 40 between proximal device node 42*p* and distal device node 42*d*.

In accordance with the inventive principles of the present disclosure, a twisting (non-whipping) threshold may be applied to the torquability metric whereby a warning of a twisting of interventional device 40 within anatomical lumen AL may be communicated to an operator or a robot navigating interventional device 40 through anatomical lumen AL if the torquability metric exceeds the twisting threshold, thereby warning the operator or the robot of a potential whipping of interventional device 40 within anatomical lumen AL (e.g., the interventional tool twisting of FIG. 8B). From the twisting warning, the operator or the robot may therefore rotate the proximal segment of the interventional device 40 extraneous to anatomical lumen AL in an opposite direction to a degree that untwists interventional device 40 within anatomical lumen AL.

Alternatively or concurrently, a whipping threshold may be applied to the torquability metric whereby a warning of a likely whipping of interventional device 40 within anatomical lumen AL may be communicated to an operator or a robot navigating interventional device 40 through anatomical lumen AL if the torquability metric exceeds the whipping threshold (e.g., the interventional tool whipping of FIG. 8C). From the whipping warning, the operator or the robot may understand a counter-rotation of the interventional device 40 within anatomical lumen AL is imperative to thereby prevent any whipping of interventional device 40 within anatomical lumen AL.

Figure 9A:
FIGS. 9A-9C illustrate a second exemplary twisting and whipping of an OSS sensor translated within an anatomical lumen as known in the art of the present disclosure.

FIG. 9A illustrates an exemplary non-twisting navigation of interventional device 40 within anatomical lumen AL involving zero rotation of proximal device node 42*p* and distal device node 42*d*.

Figure 9B:
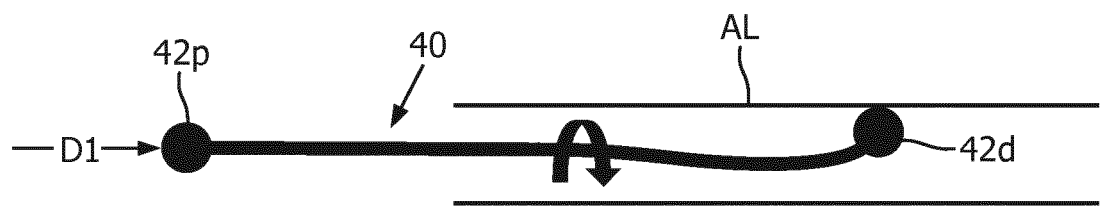
Figure 9C:
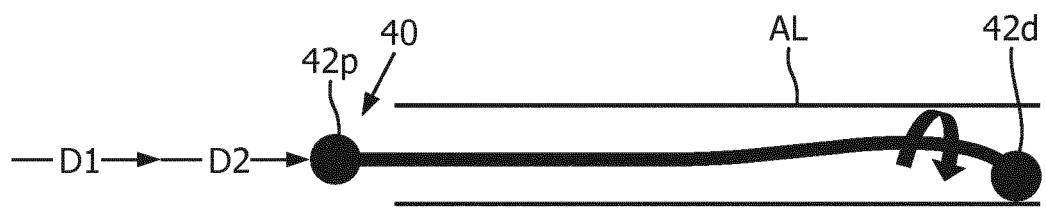

FIGS. 9B and 9C illustrate another exemplary non-folding, twisting navigation of interventional device 40 through anatomical lumen AL over distance D1 and distance D2 that involves a twisting of interventional device 40 between proximal device node 42*p* and distal device node 42*d* as a proximal segment of interventional device 40 is advanced extraneous to anatomical lumen AL. More particularly, FIG. 9B shows a non-rotation (or minimal) rotation of proximal device node 42*p* extraneous to anatomical lumen AL and a rotation of distal device node 42*d* within anatomical lumen AL (due to forces within anatomical lumen AL) as distal device node 42*d* is advanced within anatomical lumen AL that eventually results in a whipping of distal device node 42*d* within anatomical lumen as shown in FIG. 8C. In accordance with the inventive principles of the present disclosure, a pushability metric would provide an indication of a non-folding of interventional device 40 between proximal device node 42*p* and distal device node 42*d*, and a torquability metric would provide an indication of a twisting of interventional device 40 between proximal device node 42*p* and distal device node 42*d*.

Again, in accordance with the inventive principles of the present disclosure, a twisting (non-whipping) threshold may be applied to the torquability metric whereby a warning of a twisting of interventional device 40 within anatomical lumen AL may be communicated to an operator or a robot navigating interventional device 40 through anatomical lumen AL if the torquability metric exceeds the twisting threshold, thereby warning the operator or the robot of a potential whipping of interventional device 40 within anatomical lumen AL (e.g., the interventional tool twisting of FIG. 9B). From the twisting warning, the operator or the robot may therefore rotate the proximal segment of the interventional device 40 extraneous to anatomical lumen AL in an opposite direction to a degree that untwists interventional device 40 within anatomical lumen AL.

Alternatively or concurrently, a whipping threshold may be applied to the torquability metric whereby a warning of a whipping of interventional device 40 within anatomical lumen AL may be communicated to an operator or a robot navigating interventional device 40 through anatomical lumen AL if the torquability metric exceeds the whipping threshold (e.g., the interventional tool whipping of FIG. 9C). From the whipping warning, the operator or the robot may understand a counter-rotation of the interventional device 40 within anatomical lumen AL is imperative to thereby prevent any whipping of interventional device 40 within anatomical lumen AL.

For FIGS. 5A-9B, proximal device node 42*p* is located at a proximal origin of interventional device 40 and distal device node 42*d* is located at a distal tip of interventional device 40. Nonetheless, in practice of the pushability detection and the torquability detection in accordance with the present disclosure, proximal device node 42*p* and distal device node 42*d* may be located anywhere within a configuration of interventional device 40 (e.g., a tool) limited only by proximal device node 42*p* being forward of distal device node 42*d* and by distal device node 42*d* being with a segment of interventional device 40 designated to be navigated within an anatomical lumen.

Figure 10:
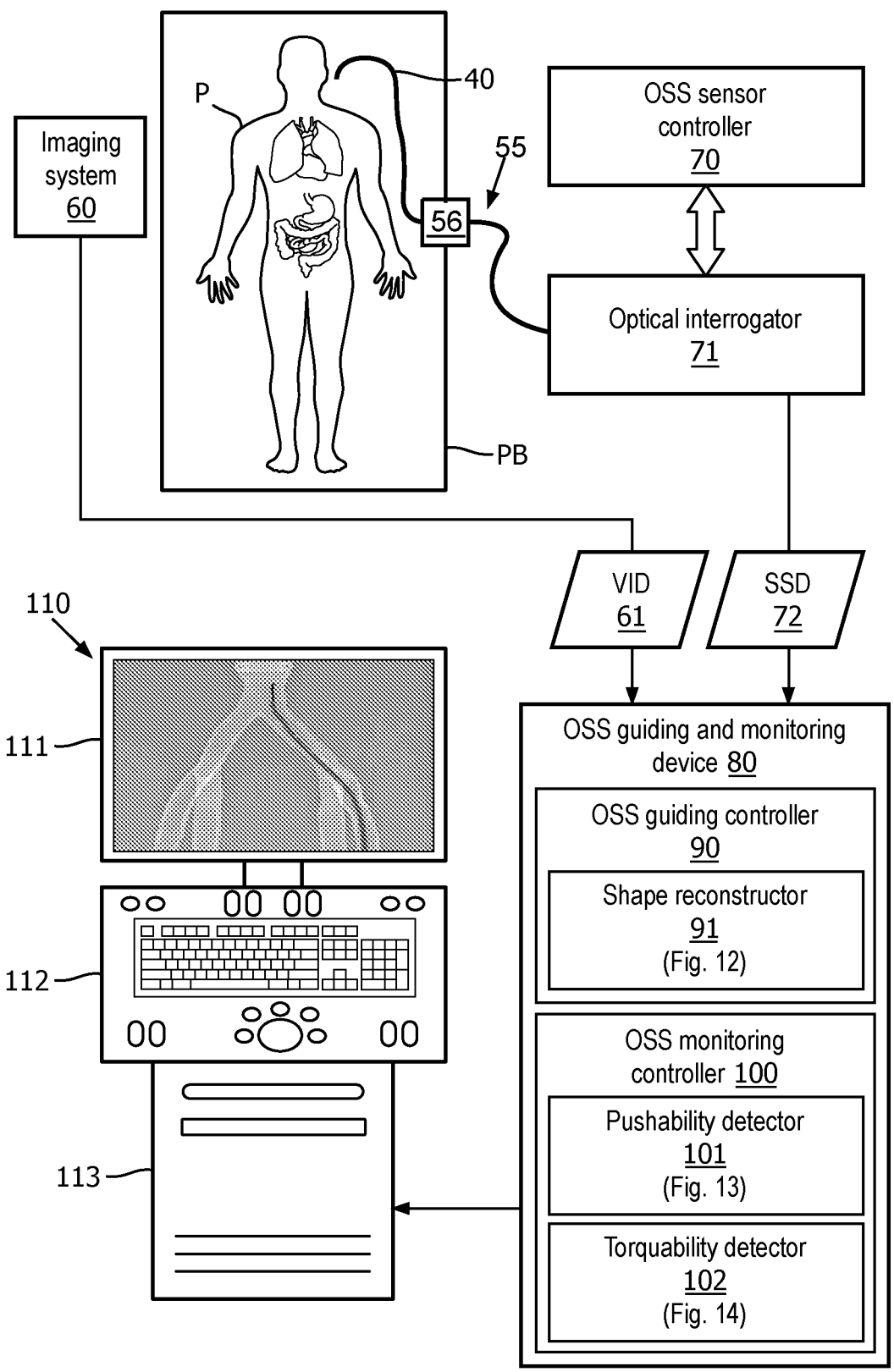
FIG. 10 illustrates an exemplary embodiment of an OSS guiding and monitoring system in accordance with the inventive principles of the present disclosure.
Figure 11A:
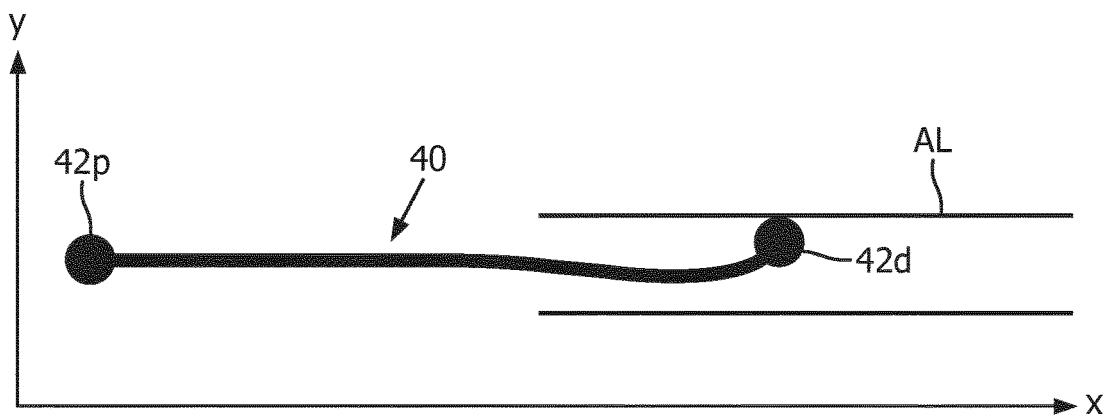
FIGS. 11A-11C illustrate exemplary guiding frames of an OSS sensor as known in the art of the present disclosure.
Figure 11B:
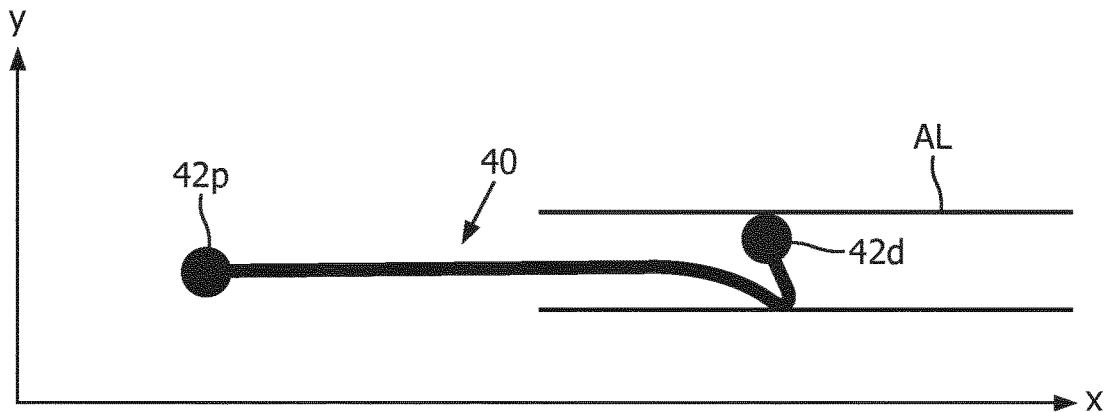
Figure 11C:
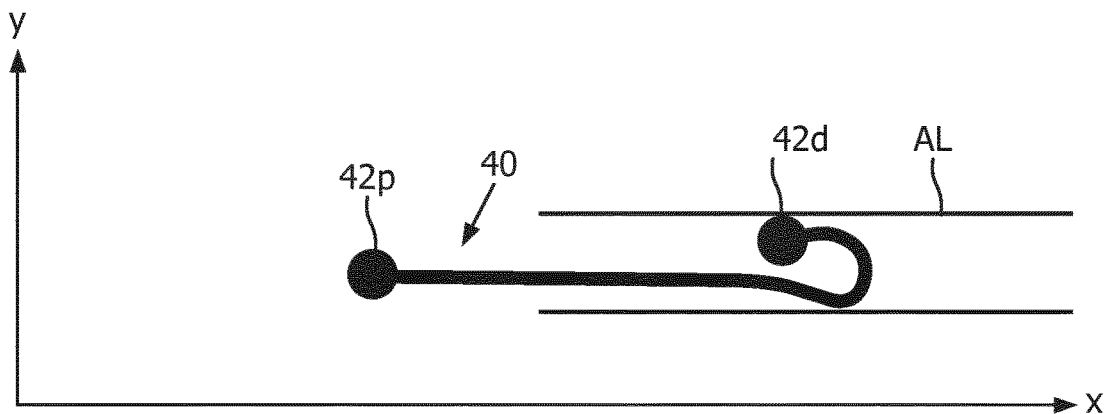
Figure 12:
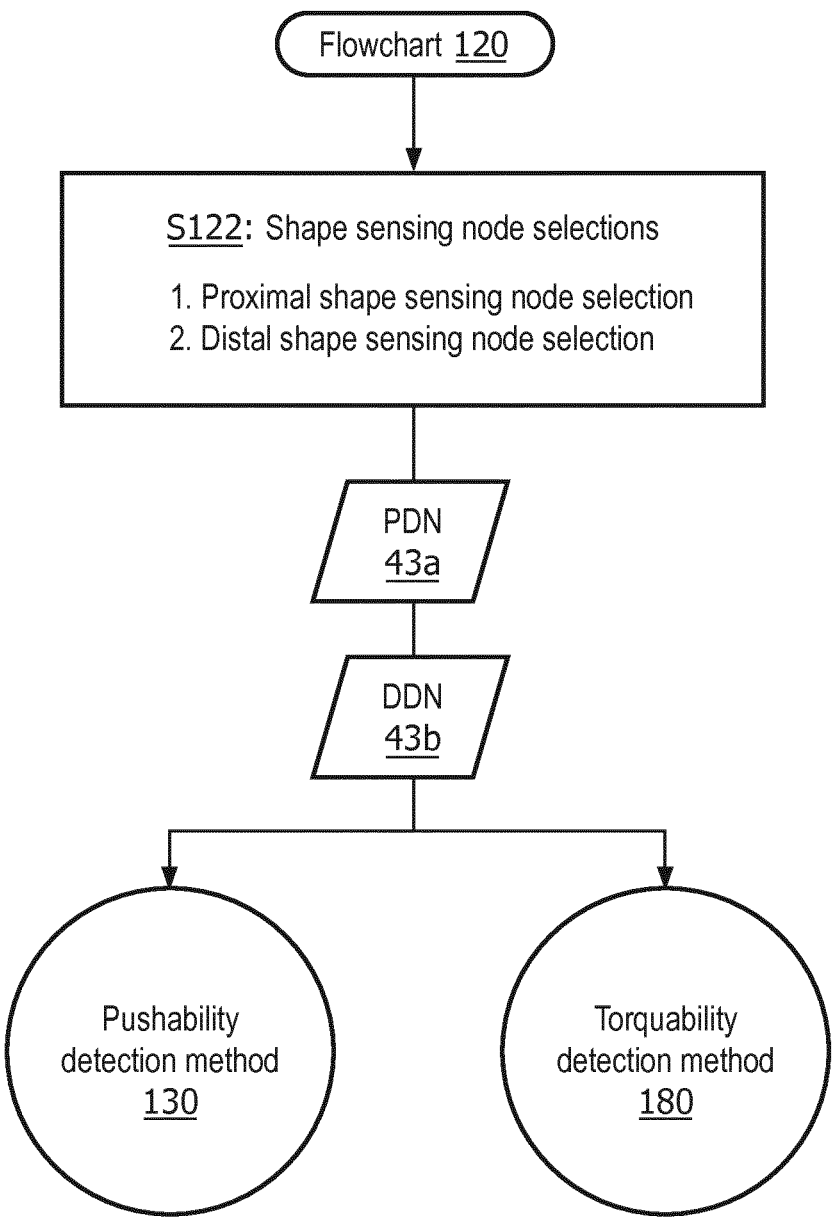
FIG. 12 illustrates a flowchart representative of an exemplary embodiment of an OSS monitoring method in accordance with the inventive principles of the present disclosure.

To facilitate a further understanding of the inventions of the present disclosure, the following description of FIGS. 10-12 teaches basic inventive principles of OSS guiding and monitoring systems, controllers and methods for a detection of any folding and/or any twisting of an interventional device, including an integration of an interventional tool and a OSS sensor, as the interventional device is navigated within an anatomical region by a linear/curvilinear translation of interventional device within the anatomical region and/or by an axial/non-axial rotation of the interventional device within the anatomical region. From this description of FIGS. 10-12, those having ordinary skill in the art will appreciate how to apply the inventive principles of the present disclosure to practice numerous and various embodiments of OSS guiding and monitoring systems, controllers and methods in accordance with the inventive principles of the present disclosure.

Referring to FIG. 10, an OSS guiding and monitoring system of the present disclosure employs an interventional device 40 (FIG. 2), an imaging system 60 and an OSS guiding and monitoring device 80 including a OSS guiding controller 90 and an OSS monitoring controller 100 installed on a workstation 110. The OSS guiding and monitoring system provides a detection of any folding and any twisting of interventional device 40 within anatomical region(s) of a patient P lying prone or otherwise on a patient bed PB (e.g., a heart and blood vessels of cardiovascular system, airways and lungs of a respiratory system, a stomach and intestines of a digestive system, and bores within of a musculoskeletal system).

In practice, interventional device 40 includes an integration of an interventional an OSS sensor 20 and one or more interventional tool(s) 30 as previously described in the present disclosure in connection with FIGS. 1-4B. For example, interventional device 40 may be OSS guidewire 40*a* (FIG. 3A), OSS guidewire 40*b* (FIG. 3B), universal catheter 40*c* (FIG. 4A) and universal catheter 40*d* (FIG. 4B).

In practice, the imaging system 60 may implement any type of imaging modality for generating volume image(s) of anatomical region(s) of patient P (e.g., a X-ray system, a MRI system, a CT system, an ultrasound system, etc.).

In practice, OSS guiding controller 90 and OSS monitoring controller 100 may embody any arrangement of hardware, software, firmware and/or electronic circuitry for guiding and monitoring a navigation of interventional device 40 within anatomical region(s) of patient P in accordance with the inventive principles of the present disclosure.

In one embodiment, OSS guiding controller 90 and OSS monitoring controller 100 may include a processor, a memory, a user interface, a network interface, and a storage interconnected via one or more system buses.

The processor may be any hardware device, as known in the art of the present disclosure or hereinafter conceived, capable of executing instructions stored in memory or storage or otherwise processing data. In a non-limiting example, the processor may include a microprocessor, field programmable gate array (FPGA), application-specific integrated circuit (ASIC), or other similar devices.

The memory may include various memories, as known in the art of the present disclosure or hereinafter conceived, including, but not limited to, L1, L2, or L3 cache or system memory. In a non-limiting example, the memory may include static random access memory (SRAM), dynamic RAM (DRAM), flash memory, read only memory (ROM), or other similar memory devices.

The user interface may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface.

The network interface may include one or more devices, as known in the art of the present disclosure or hereinafter conceived, for enabling communication with other hardware devices. In a non-limiting example, the network interface may include a network interface card (NIC) configured to communicate according to the Ethernet protocol. Additionally, the network interface may implement a TCP/IP stack for communication according to the TCP/IP protocols. Various alternative or additional hardware or configurations for the network interface will be apparent.

The storage may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage may store instructions for execution by the processor or data upon with the processor may operate. For example, the storage may store a base operating system for controlling various basic operations of the hardware. The storage may further store one or more application modules in the form of executable software/firmware.

More particularly, still referring to FIG. 10, an application module of OSS guiding controller 90 is a shape reconstructor 91 for reconstructing a shape of interventional device 40 in response to shape sensing data 72 as known in the art of the present disclosure and further exemplary described in the present disclosure.

Further, application modules of OSS monitoring controller 100 include a pushability detector 101 for detecting any folding of interventional device 40 within anatomical region(s) of patient P in accordance with the inventive principles of the present disclosure as will be further exemplarily described in the present disclosure, and/or a torquability detector 102 for detecting any twisting of interventional device 40 within anatomical region(s) of patient P in accordance with the inventive principles of the present disclosure as will be further exemplarily described in the present disclosure.

In practice, OSS monitoring controller 100 may include pushability detector 101 and/or torquability detector 102.

Still referring to FIG. 10, workstation 110 includes a known arrangement of a monitor 111, a keyboard 112 and a computer 113.

In practice, OSS guiding and monitoring device 80 may be alternatively or concurrently installed on other types of processing devices including, but not limited to, a tablet or a server accessible by workstations and tablets, or may be distributed across a network supporting an execution of interventional procedures involving interventional device 40.

Also in practice, OSS guiding controller 90 and OSS monitoring controller 100 may be integrated components, segregated components or logically partitioned components of OSS guiding and monitoring device 80.

Still referring to FIG. 10, in operation, imaging system 60 pre-operatively and/or intra-operatively generates volume image data VID 61 for displaying a volume image of the subject anatomical region(s) of patient P. Volume image data VID 61 is communicated to OSS guiding and monitoring device 80 (e.g., a streaming or an uploading of volume image data VID 61) whereby OSS guiding controller 90 may control an overlay display of a reconstructed shape of interventional device 40 on the volume image of anatomical region(s) of patient P as known in the art of the present disclosure. For example, FIG. 10 illustrates an overlay display on monitor 111 of a reconstructed shape of interventional device 40 on a volume image of vasculature of patient P.

Alternatively, the OSS guiding and monitoring system may omit imaging system 60 whereby only a reconstruction shape of interventional device 40 may be displayed on monitor 111.

Interventional device 40 distally extends from a launch 56 adjoined to a rail of patient bed PB as shown, or alternatively adjoined to a cart (not shown) next to patient bed PB or alternatively adjoined to a workstation (e.g., OSS monitoring controller 100 or a tablet (not shown)). An optical fiber 55 proximally extends from launch 56 to an optical interrogator 71. In practice, optical fiber 55 may be a separate optical fiber connected to OSS sensor 20 of interventional device 40 at launch 56, or a proximal extension of OSS sensor 20 extending through launch 56.

As known in the art of the present disclosure, an OSS sensor controller 70 controls a cyclical emission of light by optical interrogator 71 via optical fiber 55 into OSS sensor 20 whereby the light is propagated through OSS sensor 20 to a distal tip of interventional device 40 to thereby generate shape sensing data 72 informative of a shape of interventional device 40 relative to launch 56 serving as a fixed reference position. In practice, the distal end of OSS sensor 20 may be closed, particularly for light reflective embodiments of OSS sensor 20, or may be opened, particularly for light transmissive embodiments of OSS sensor 20.

OSS sensor controller 70 controls a communication of a temporal frame sequence of shape sensing data 72 to OSS guiding controller 90 as known in the art of the present disclosure. More particularly, each frame consists of a single interrogation cycle of the strain sensors of OSS sensor 20 (e.g., Fiber Bragg Gratings or Rayleigh backscatter) whereby shape reconstructor 91 reconstructs a shape of OSS sensor 20 on a temporal frame basis as known in the art of the present disclosure, which provides for a reconstruction of a shape of interventional device 40 derived from the particular integration of OSS sensor 20 and interventional device(s) 30.

In practice, shape reconstructor 91 may implement any reconstruction technique for reconstructing the shape of interventional device 40 as known in the art of the present disclosure.

In one reconstruction embodiment, shape reconstructor 91 executes a delineation of pose of a shape of interventional device 40 via shape sensing data 72 on a temporal frame basis within a coordinate system corresponding to optical interrogator 71.

In a second reconstruction embodiment, shape reconstructor 91 executes a registration of a coordinate system of optical interrogator 71 to a coordinate system of imaging system 60 whereby shape reconstructor 91 may position and orientate a delineation of a shape of interventional device 40 via shape sensing data 72 on a temporal frame basis within the coordinate system of imaging system 60. For example, FIGS. 11A-11C illustrates a reconstruction of a shape of interventional device 40 within a coordinate system of imaging system 60 on a temporal frame basis including the exemplary navigation of interventional device 40 within anatomical lumen AL as shown in FIGS. 6A-6C.

Referring back to FIG. 10, as OSS guiding controller controls a display of the reconstructed shape of interventional device 40, OSS monitoring controller 100 implements an OSS monitoring method of the present disclosure as represented by a flowchart 120 shown in FIG. 12.

Referring to FIG. 12, a stage S122 of flowchart 120 encompasses OSS monitoring controller 100 implementing a static or a dynamic selection of a proximal device node and a distal device node of interventional device 40.

In practice, OSS monitoring controller 100 may implement any technique as known in the art of the present disclosure for selecting a device node as a single point, multiple points, a segment, a template (e.g., shape, curvature or strain) or otherwise any portion of interventional device 40.

In one embodiment of stage S122, a graphical user interface is provided to an operator of workstation 110 subsequent to a registration of interventional device 40 and imaging system 60 whereby the operator is able to select the proximal device node and the distal device node.

In another embodiment of stage S122, a distal OSS node at or adjacent a distal tip of OSS sensor 20 is designated by OSS monitoring controller 100 as the distal device node.

In another embodiment of stage S122, OSS monitoring controller 100 designates the proximal device node by either (1) using a registered position of interventional device 40 (e.g., a universal catheter position), (2) identifying where an operator is holding interventional device 40 (e.g., via a temperature profile measured in the axial strain or via a curvature signature due to the grasping of OSS sensor 20 as known in the art of the present disclosure), or (3) identifying where interventional device 40 enters the body of patient P (e.g., via a temperature profile and/or a shape template of an introducer as known in the art of the present disclosure).

OSS monitoring controller 100 provides proximal device node selection data 43a and distal device node selection data 43b to pushability detector 101 for the execution of a pushability detection method 130 in accordance with the inventive principles of the present disclosure and/or provides proximal device node selection data 43a and distal device node selection data 43b to torquability detector 102 for the execution of a torquability detection method 180 in accordance with the inventive principles of the present disclosure.

More particularly as to pushability detection method 130, pushability detector 101 derives one or more pushability metrics via shape sensing data 72 (FIG. 10) on a temporal frame basis by detecting:

1. an advancement of the proximal device node of interventional device 40 extraneous to the anatomical region without a corresponding advancement of the distal device node of interventional device 40 within the anatomical region of patient P;
2. a region of a longitudinal curvature change of interventional device 40 between the proximal device node and the distal device node of interventional device 40 as interventional device 40 is navigated within the anatomical region of patient P;
3. excessive forces on the distal device node of interventional device 40 as interventional device 40 is navigated within the anatomical region of patient P; and/or
4. excessive transverse motion by interventional device 40 as interventional device 40 is navigated within the anatomical region of patient P.

For folding/buckling warning purposes, pushability detector 101 may ascertain a potential for a buckling of interventional device 40 responsive to a pushability metric having a non-zero magnitude exceeding a folding (non-buckling threshold) delineating a folding of interventional device 40 whereby the interventional tool is capable of being further advanced within the anatomical region, and/or the pushability metric having a non-zero magnitude exceeding a buckling threshold delineating a folding of the interventional device whereby interventional device 40 is incapable of being further advanced within the anatomical region.

A folding warning and/or a buckling warning may be communicated by pushability detector 101 by:

1. a textual display warning (e.g., a textual folding/buckling message overlaying a displayed shape reconstruction of the interventional device),
2. an auditory warning (e.g., an auditory message verbalizing a folding or a buckling of the interventional device);
3. a visual display warning (e.g., a color encoded folding/buckling warning of a displayed shape reconstruction of the interventional device);
4. a visual device warning (e.g., an energizing of a hub LED of the interventional device), and
5. a haptic warning (e.g., a vibration of a hub motor of interventional device).

More particularly as to torquability detection method 180, torquability detector 102 derives one or more torquability metrics via shape sensing data 72 (FIG. 10) on a temporal frame basis by detecting:

1. a rotation of the proximal device node of OSS sensor 20 extraneous to the anatomical region of patient P without a corresponding rotation of the distal device node of OSS sensor 20 within the anatomical region of patient P; and
2. a region of an axial rotation of OSS sensor 20 between the proximal device node of OSS sensor 20 and the distal device node of OSS sensor 20 as interventional device 40 is navigated within the anatomical region of patient P.

For twisting/whipping warning purposes, torquability detector 102 may ascertain a potential for a whipping of interventional device 40 responsive to the torquability metric having a non-zero magnitude or exceeding a twisting (non-whipping) threshold delineating a twisting of the interventional device insusceptible to a whipping of interventional device 40 within the anatomical region, and/or the torquability metric having a non-zero magnitude exceeding a whipping threshold indicative of a delineated twisting of interventional device 40 susceptible to a whipping of the interventional device within the anatomical region.

A twisting waring and/or or a whipping warning may be communicated by torquability detector 102 by:

1. a textual display warning (e.g., a textual twisting/whipping message overlaying a displayed shape reconstruction of the interventional device),
2. an auditory warning (e.g., an auditory message verbalizing a twisting or a whipping of the interventional device);
3. a visual display warning (e.g., a color encoded twisting/whipping warning of a displayed shape reconstruction of the interventional device);
4. a visual device warning (e.g., an energizing of a hub LED of the interventional device), and
5. a haptic warning (e.g., a vibration of a hub motor of interventional device).

To facilitate a further understanding of the inventions of the present disclosure, the following description of FIGS. 13-16 teaches embodiments of a pushability detection method and a torquability detection method in accordance with the inventive principles of the present invention. From this description of FIGS. 13-16, those having ordinary skill in the art will appreciate how to apply the inventive principles of the present disclosure to practice numerous and various embodiments of pushability detection methods and torquability detection methods in accordance with the inventive principles of the present invention.

Figure 13A:
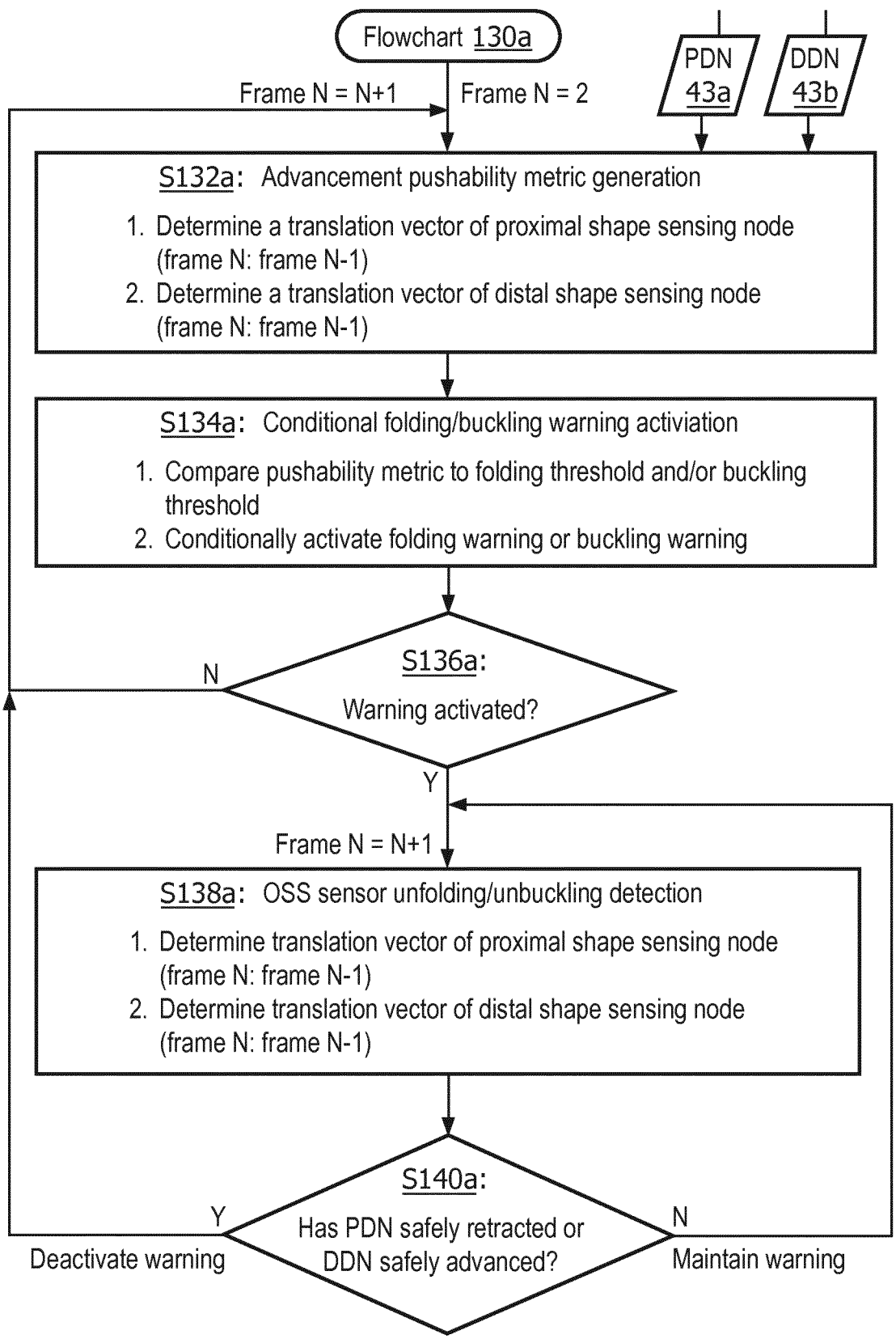
FIG. 13A illustrates a flowchart representative of an exemplary embodiment of an advancement pushability monitoring method in accordance with the inventive principles of the present disclosure.

Referring to FIG. 13A, a flowchart 130a represents one embodiment of pushability detection method 130 (FIG. 12) executable by pushability detector 101 (FIG. 10) on a temporal frame basis as a proximal segment of interventional device 40 (FIG. 10) is being manually or robotically advanced into an anatomical region.

A stage S132a of flowchart 130a encompasses an initial generation of an advancing pushability metric by pushability detector 101 in response to two (2) or more frames of shape sensing data 72 (FIG. 10) corresponding to a proximal device node as indicated by proximal device node selection data 43a and a distal device node as indicated by distal device node selection data 43b. More particularly, stage S132a involves a determination by pushability detector 101 of a translation vector $TV_{PSSN}$ of the proximal device node within the associated coordinate system (e.g., interrogator or imaging) and a translation vector $TV_{DSSN}$ of the distal device node within the associated coordinate system (e.g., interrogator or imaging) whereby the pushability metric is a differential between the magnitude of the two vectors in accordance with $TV_{PSSN}$-$TV_{DSSN}$.

A stage S134a of flowchart 130a encompasses a conditional activation of a folding warning based on an application of a folding threshold to the pushability metric and/or a conditional activation of a buckling warning based on an application of a buckling threshold to the pushability metric. More particularly, the folding threshold delineates a folding of the interventional device whereby interventional device 40 is capable of being further advanced within the anatomical region, and/or the buckling threshold delineates a folding of interventional device 40 whereby the interventional tool is incapable of being further advanced within the anatomical region.

In practice, either the folding threshold and/or the buckling threshold may be implemented by pushability detector 101.

If the folding threshold is exclusively implemented by pushability detector 101, then the folding threshold may be any magnitude greater than zero whereby a folding warning will be activated when the pushability metric exceeds the folding threshold. The folding warning may be communicated by pushability detector 101 via a color encoding of the displayed reconstructed shape of interventional device 40 within the anatomical region of patient P, a textual display warning, an auditory warning, a visual warning (e.g., an energizing of a hub LED of interventional device 40) and/or haptic feedback (e.g., a vibration of a hub motor of interventional device 40).

In practice, the value of the folding threshold may be derived from a machine learning or empirically from a plurality of test scenarios.

Similarly, if the buckling threshold is exclusively implemented by pushability detector 101, then the buckling threshold may be any magnitude greater than zero whereby a buckling warning will be activated when the pushability metric exceeds the buckling threshold. The buckling warning may be communicated by pushability detector 101 via a color encoding of the displayed reconstructed shape of interventional device 40 within the anatomical region of patient P, a textual display warning, an auditory warning, a visual warning (e.g., an energizing of a hub LED of interventional device 40) and/or haptic feedback (e.g., a vibration of a hub motor of interventional device 40).

In practice, the value of the buckling threshold may be derived from a machine learning or empirically from a plurality of test scenarios.

Otherwise, if the both the folding threshold and the buckling threshold are implemented by pushability detector 101, then the folding threshold will have a magnitude greater than zero and less than a magnitude of the buckling threshold whereby a folding warning will be activated when the pushability metric exceeds the folding threshold yet is less than the buckling threshold and whereby a buckling warning will be activated when the pushability metric exceeds the buckling threshold. The folding warning and the buckling warning may be communicated by pushability detector 101 as previously described in the present disclosure with each warning having a distinctive mode. For example, an activated folding warning may periodically energize a hub LED while an activated buckling warning may fully energize the hub LED. Also, by example, an activated folding warning may periodically vibrate a hub motor while an activated buckling warning continually vibrates the hub motor.

An example of a non-activated warning scenario is shown in FIGS. 5A-5C.

Examples of an activated warning scenario is shown in FIGS. 6A-6C and 7A-7C.

Referring still to FIG. 13A, if a warning is not activated during stage S134a as ascertained by pushability detector 101 during a stage S136a of flowchart 130a, then pushability detector 101 returns to stage S132a to process a next set of frames of proximal device node and distal device node.

Otherwise, if a warning is activated during stage S134a as ascertained by pushability detector 101 during stage S136a, then pushability detector 101 proceeds to a stage S138a of flowchart 130a encompassing a determination by pushability detector 101 of a translation vector $TV_{PSSN}$ of the proximal device node within the associated coordinate system (e.g., interrogator or imaging) and a translation vector $TV_{DSSN}$ of the distal device node within the associated coordinate system (e.g., interrogator or imaging) whereby the pushability metric is a differential between the magnitude of the two vectors in accordance with $TV_{PSSN}-TV_{DSSN}$.

If the pushability detector 101 ascertains during a stage S140a of flowchart 130a that a direction and a magnitude of translation vector $TV_{PSSN}$ of the proximal device node indicates the proximal device node has been retracted relative to the anatomical region to a degree exceeding the folding threshold or the buckling threshold (whichever is applicable to the activated warning), or if the pushability detector 101 ascertains during stage S140 that a direction and a magnitude of translation vector $TV_{DSSN}$ of the distal device node indicates the distal device node has been advanced within the anatomical region to a degree exceeding the folding threshold or the buckling threshold (whichever is applicable to the activated warning), or if the pushability detector 101 ascertains during stage S140 any combination of proximal retraction and distal advancement exceeding the folding threshold or the buckling threshold (whichever is applicable to the activated warning), then pushability detector 101 deactivates the activated warning and returns to stage S132a to process a next set of frames of proximal device node and distal device node.

Otherwise, pushability detector 101 returns to stage S138a to process a next set of frames of proximal device node and distal device node until such time the proximal sensing strain node has been safely retracted and/or the distal sensing strain node has been safely advanced.

Examples of a safe proximal sensing strain node retraction is shown in FIGS. 6A-6C and 7A-7C in reverse order.

In an alternative embodiment of flowchart 130a, stage S134a may further involve an additional conditional activation of a warning. In one version of this alternative embodiment of flowchart 130a, if the advancement pushability metric does not exceed an applicable threshold (i.e., the distal device node had a corresponding advancement as the proximal device node), then pushability detector 101 may nonetheless activate a folding/buckling warning if the shape of a region of OSS sensor 20 including the distal device node conforms to a template pushability metric in the form of a folding template or a buckling template of OSS sensor 20 derived from shape, curvature or strain information of OSS sensor 20 (e.g., a C-shaped template or a Z-shaped template).

In another version of this alternative embodiment, if the advancement pushability metric does not exceed an applicable threshold (i.e., the distal device node had a corresponding advancement as the proximal device node), then pushability detector 101 may nonetheless activate a folding/buckling warning if a monitored spatial positioning of between any two (2) OSS nodes of OSS sensor 20 between the proximal device node and the distal device node of interventional device 40 is less than a spatial threshold derived from a structural spatial positioning of the adjacent OSS nodes of OSS sensor 20 in a straight alignment. For example, adjacent OSS nodes of OSS sensor 20 may have a structural spatial positioning of X (e.g., a spatial distance in centimeters) whereby a folding/buckling warning is activated if a monitored spatial positioning Y of any two (2) OSS nodes of OSS sensor 20 is less than a spatial threshold Z (e.g., a spatial distance in millimeters).

Still referring to FIG. 13A, those skilled in the art of the present disclosure will appreciate that a benefit of flowchart 130a is a systematic of a conditional activation of a warning of a potential or a likely buckling of interventional device 40.

Figure 13B:
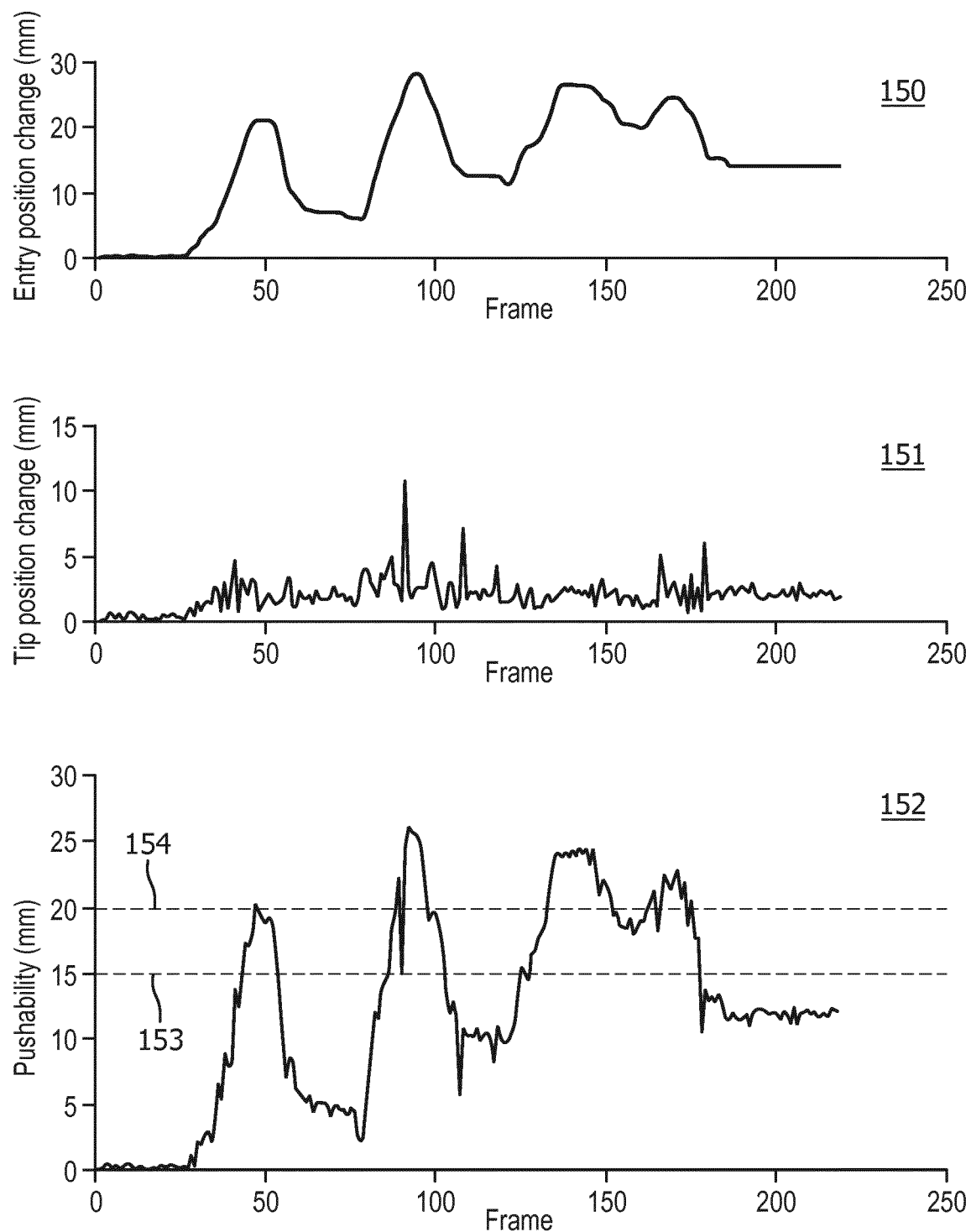
FIG. 13B illustrates exemplary graphs of a proximal device node translation, a distal device node translation and a pushability metric generated by an execution of the advancement pushability monitoring method of FIG. 13A.

For example, FIG. 13B illustrates a temporal graph 150 of an exemplary translation vector $TV_{PSSN}$ of a proximal device node at an entry position of the anatomical region, a temporal graph display 151 of an exemplary translation vector $TV_{DSSN}$ of the distal device node at a distal tip of OSS sensor 20, and a temporal graph of an exemplary pushability metric being a differential $TV_{PSSN}$–$TV_{DSSN}$. An exemplary folding threshold 153 and/or an exemplary buckling threshold 154 may be applied to the pushability metric for the conditional activation of a warning of a potential or a likely buckling of interventional device 40.

Referring back to FIG. 13A, a warning activation during stage S134a may involve a determination by pushability detector 101 of a location of any folding or any buckling of OSS sensor 20 as indicated by a curvature of adjacent nodes of OSS sensor 20.

Figure 14A:
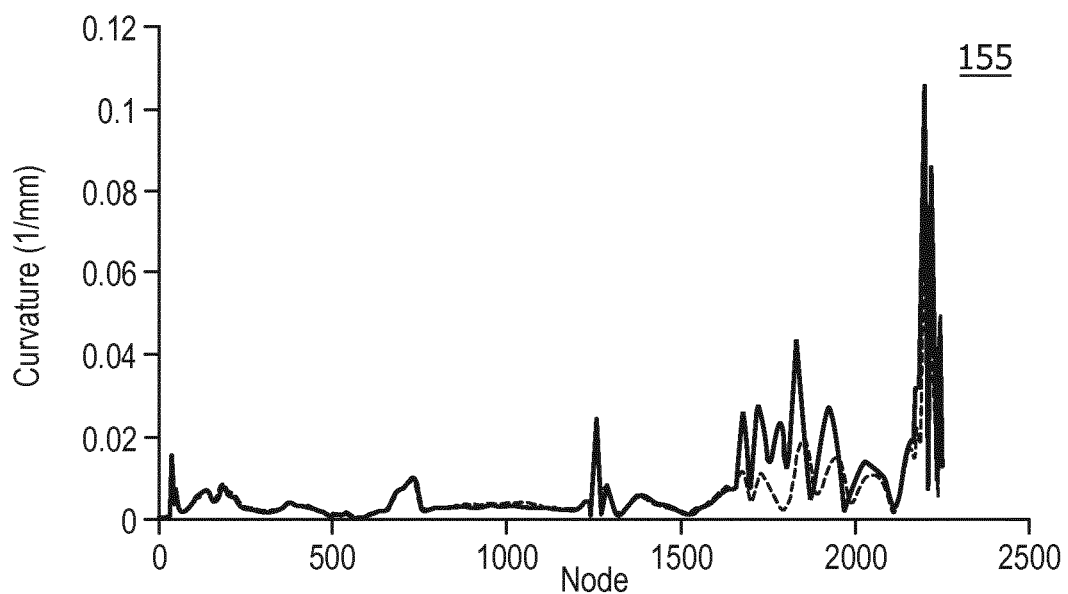
FIGS. 14A and 14B illustrate exemplary graphs of a guiding display of the OSS sensor highlighting a folding region of the OSS sensor in accordance with the inventive principles of the present disclosure.
Figure 14B:
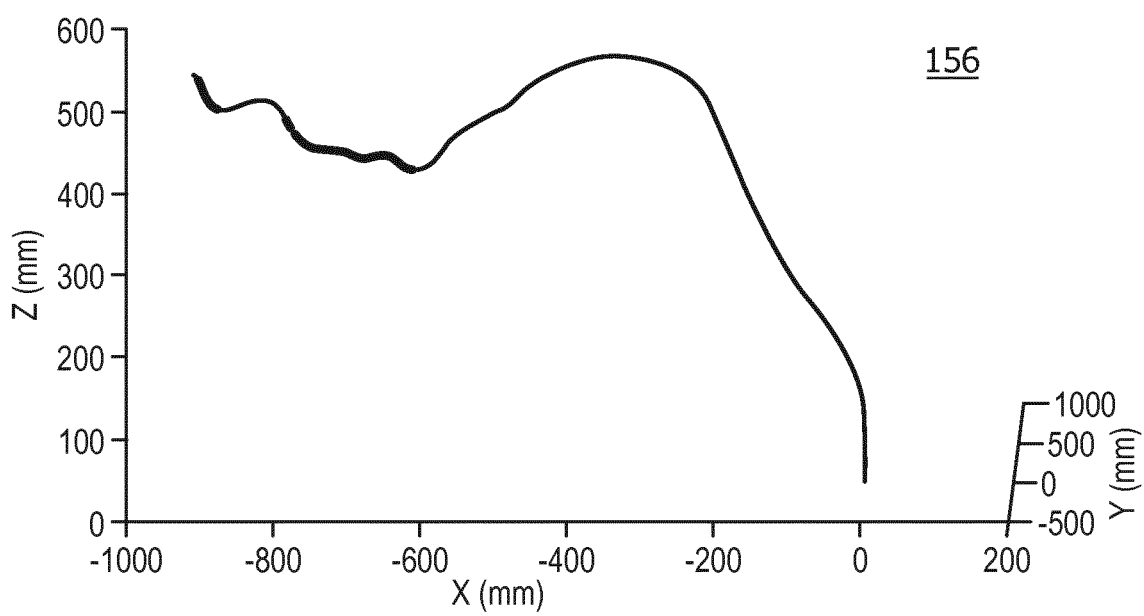

For example, FIG. 14A illustrates a nodal graph 155 of a curvature of OSS sensor 20 extending from a most proximal node to a most distal node whereby a high curvature of OSS sensor 20 along the distal segment of OSS sensor 20 corresponds to a detected folding and/or a detected buckling of OSS sensor 20 during a frame 95 of the pushability metric shown in FIG. 13B. This detected folding and/or detected buckling may be communicated to an operator via a plot of the reconstructed shape of OSS sensor 20/interventional device 40, such as, for example, by an exemplary identification of a potential buckling via a plot 156 of the reconstructed shape of OSS sensor 20/interventional device 40 as shown in FIG. 14B.

In practice, a location of a region of folding and/or buckling of interventional device 40 as sensed by OSS sensor 20 may be communicated to the operator by a changing of a visualization of the shape of interventional device 40 in that region (color-coding, blinking, thicker shape visualization, etc.), or by a small window in the bottom of the monitor screen showing the whole shape and highlighting the regions with buckling (useful with the user field-of-view is small and the buckling is unlikely to occur in that region), or by automatically zooming the operator over the region of the buckling (may also be done upon the user selecting this option), or by deleting the entire shape of interventional device 40 from view and displaying a warning to the user.

Figure 15:
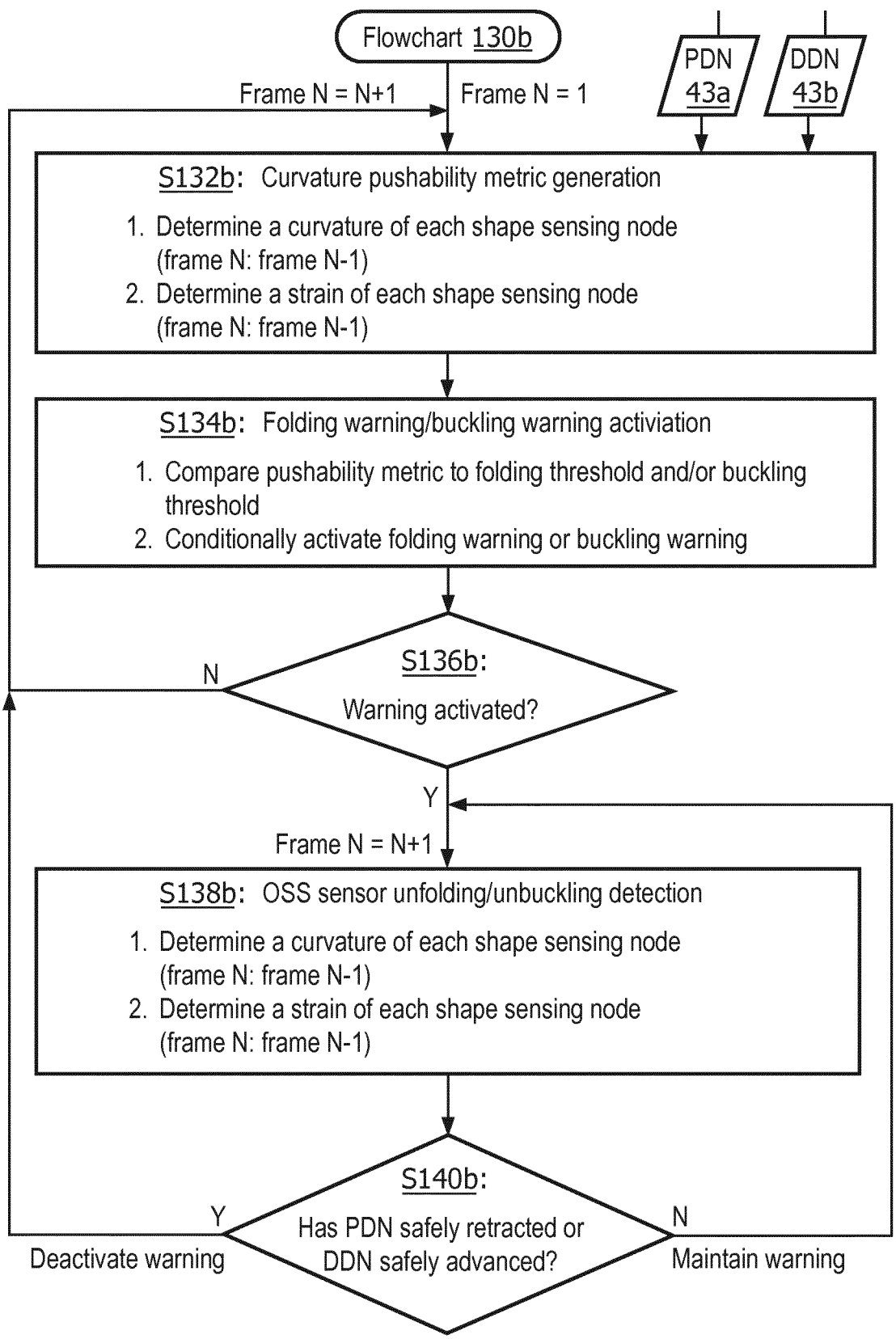
FIG. 15 illustrates a flowchart representative of an exemplary embodiment of a curvature pushability monitoring method in accordance with the inventive principles of the present disclosure.

Referring to FIG. 15, a flowchart 130b represents one embodiment of pushability detection method 130 (FIG. 12) executable by pushability detector 101 (FIG. 10) on a temporal frame basis as a proximal segment of interventional device 40 (FIG. 10) is being manually or robotically advanced into an anatomical region.

A stage S132b of flowchart 130b encompasses an initial generation of a curvature pushability metric by pushability detector 101 in response to two (2) frames of shape sensing data 72 (FIG. 10) corresponding to a proximal device node as indicated by proximal device node selection data 43a and a distal device node as indicated by distal device node selection data 43b.

In one embodiment, stage S132b involves a determination by pushability detector 101 of a curvature of each device node between the proximal device node and the distal device node within the associated coordinate system (e.g., interrogator or imaging) for each frame whereby a node curvature pushability metric for each node is a differential between the curvature of particular node over the two frames.

In another embodiment, stage S132b involves a determination by pushability detector 101 of a strain of each device node between the proximal device node and the distal device node within the associated coordinate system (e.g., interrogator or imaging) for each frame whereby a strain curvature pushability metric for each node is a differential between a strain on a particular node over the two frames.

A stage S134b of flowchart 130b encompasses a conditional activation of a folding warning based on an application of a folding threshold to the pushability metric (node curvature or strain curvature) and/or a conditional activation of a buckling warning based on an application of a buckling threshold to the pushability metric (node curvature or strain curvature). More particularly, the folding threshold delineates a folding of the interventional device whereby interventional device 40 is capable of being further advanced within the anatomical region, and/or the buckling threshold indicative delineates a folding of interventional device 40 whereby the interventional tool is incapable of being further advanced within the anatomical region.

In practice, the folding threshold and/or the buckling threshold may be implemented by pushability detector 101.

If the folding threshold is exclusively implemented by pushability detector 101, then the folding threshold may be any magnitude greater than zero whereby a folding warning will be activated when the pushability metric (node curvature or strain curvature) exceeds the folding threshold. The folding warning may be communicated by pushability detector 101 via a textual display warning, an auditory display warning, a visual display warning (e.g., color encoding of a displayed overlay of interventional device 40), a visual device warning (e.g., an energizing of a hub LED of interventional device 40) and/or haptic device warning (e.g., a vibration of a hub motor of interventional device 40) as previously described herein.

In practice, the value of the folding threshold may be derived from a machine learning or empirically from a plurality of test scenarios.

Similarly, if the buckling threshold is exclusively implemented by pushability detector 101, then the buckling threshold may be any magnitude greater than zero whereby a buckling warning will be activated when (node curvature or strain curvature) exceeds the buckling threshold. The buckling warning may be communicated by pushability detector 101 via a textual display warning, an auditory display warning, a visual display warning (e.g., color encoding of a displayed overlay of interventional device 40), a visual device warning (e.g., an energizing of a hub LED of interventional device 40) and/or haptic device warning (e.g., a vibration of a hub motor of interventional device 40) as previously described herein.

In practice, the value of the buckling threshold may be derived from a machine learning or empirically from a plurality of test scenarios.

Otherwise, if the both the folding threshold and the buckling threshold are implemented by pushability detector 101, then the folding threshold will have a magnitude greater than zero and less than a magnitude of the buckling threshold whereby a folding warning will be activated when (node curvature or strain curvature) exceeds the folding threshold yet is less than the buckling threshold and whereby a buckling warning will be activated when (node curvature or strain curvature) exceeds the buckling threshold. The folding warning and the buckling warning may be communicated by pushability detector 101 as previously described in the present disclosure with each warning having a distinctive mode. For example, an activated folding warning may periodically energize a hub LED while an activated buckling warning may fully energize the hub LED. Also, by example, an activated folding warning may periodically vibrate a hub motor while an activated buckling warning continually vibrates the hub motor.

An example of a non-activated warning scenario is shown in FIGS. 5A-5C.

Examples of an activated warning scenario is shown in FIGS. 6A-6C and 7A-7C.

In practice, a folding warning may be activated at an increasing intensity and an increasing frequency as the pushability metric increasingly exceeds the folding threshold or as the pushability metric approaches the folding threshold.

Also in practice, a buckling warning may be activated at an increasing intensity and an increasing frequency as the pushability metric increasingly exceeds the buckling threshold or as the pushability metric approaches the buckling threshold.

Referring still to FIG. 15, if a warning is not activated during stage S134b as ascertained by pushability detector 101 during a stage S136b of flowchart 130b, then pushability detector 101 returns to stage S132b to process a next set of frames of proximal device node and distal device node.

Otherwise, if a warning is activated during stage S134b as ascertained by pushability detector 101 during stage S136b, then pushability detector 101 proceeds to a stage S138b of flowchart 130b.

In one embodiment, stage S138b involves a determination by pushability detector 101 of a curvature of each device node between the proximal device node and the distal device node within the associated coordinate system (e.g., interrogator or imaging) for each frame whereby a node curvature pushability metric for each node is a differential a between the curvature of particular node over the two frames.

In another embodiment, stage S138b involves a determination by pushability detector 101 of a strain of each device node between the proximal device node and the distal device node within the associated coordinate system (e.g., interrogator or imaging) for each frame whereby a strain curvature pushability metric for each node is a differential a between a strain on a particular node over the two frames.

If the pushability detector 101 ascertains during a stage S140b of flowchart 130b that the pushability metric(s) (node curvature or strain curvature) driving the activation the warning are now indicting the proximal device node has been retracted relative to the anatomical region to a degree exceeding the folding threshold or the buckling threshold (whichever is applicable to the activated warning), or if the pushability detector 101 ascertains during stage S140 that the pushability metric(s) (node curvature or strain curvature) driving the activation the warning are now indicting the distal device node has been advanced within the anatomical region to a degree exceeding the folding threshold or the buckling threshold (whichever is applicable to the activated warning), or if the pushability detector 101 ascertains during stage S140 any combination of proximal retraction and distal advancement exceeding the folding threshold or the buckling threshold (whichever is applicable to the activated warning), then pushability detector 101 deactivates the activated warning and returns to stage S132b to process a next set of frames of the device nodes between the proximal device node and distal device node.

Otherwise, pushability detector 101 returns to stage S138b to process a next set of frames of the device nodes between the proximal device node and distal device node until such time the proximal sensing strain node has been safely retracted and/or the distal sensing strain node has been safely advanced.

Examples of a safe proximal sensing strain node retraction is shown in FIGS. 6A-6C and 7A-7C in reverse order.

Figure 16:
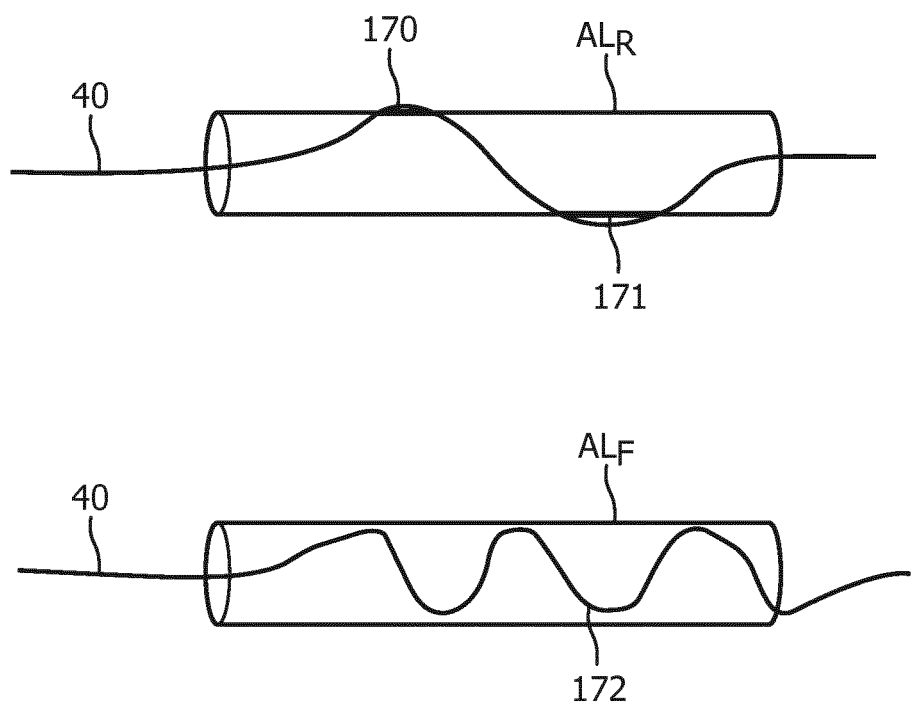
FIG. 16 illustrates an exemplary excessive transverse motion of an OSS sensor detected by an execution of the curvature pushability monitoring method of FIG. 15.

In an alternative embodiment of flowchart 130b, stage S134b may further involve an additional conditional activation of a warning. Specifically, transverse and friction forces may be applied to the anatomical region with a folding, particularly a buckling, of interventional device 40 within a rigid anatomical region. For example, FIG. 16 illustrates a natural mechanical path 170 of interventional device 40 that is limited to a constrained path 171 within rigid anatomical lumen $AL_R$.

To detect such transverse and friction forces, stage S132b involves pushability detector 101 deriving a path curvature pushability metric from registered volume imaging data 61 (FIG. 10) to thereby delineate a rigid path through the anatomical region, and stage S134b involves pushability detector 1010 comparing the path curvature pushability metric to the curvature profile of interventional device 40 on a frame by frame basis. A buckling warning is activated if the comparison indicates the anatomical region is constraining a natural mechanical path of interventional device 40 through the anatomical lumen (e.g., via a spline interpolation of interventional device 40 as known in the art of the present disclosure).

Referring back to FIG. 15, those skilled in the art of the present disclosure will appreciate that a benefit of flowchart 130b is a systematic conditional activation of a warning of a potential or a likely buckling of interventional device 40.

Figure 17A:
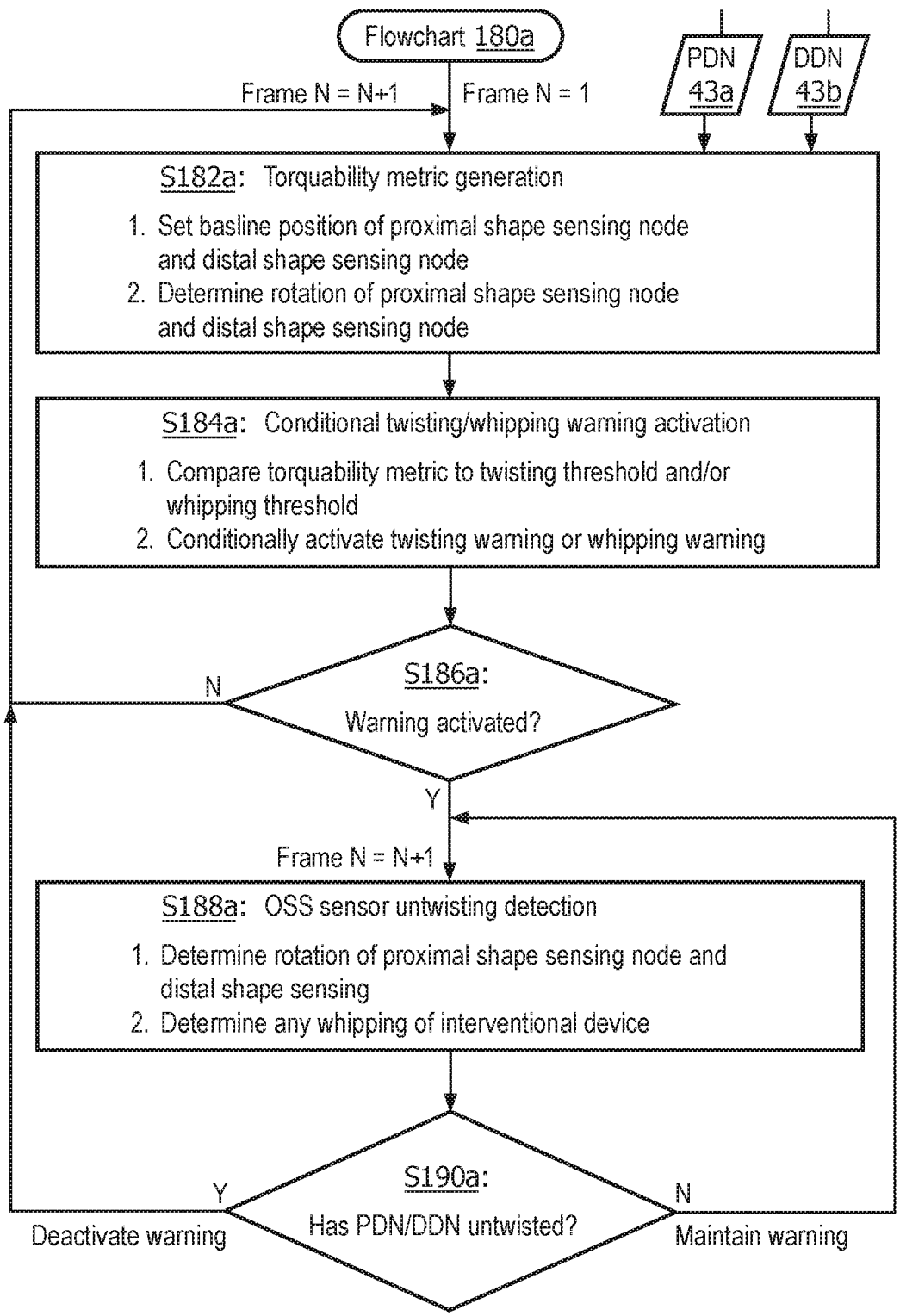
FIG. 17A illustrates a flowchart representative of an exemplary embodiment of a torquability monitoring method in accordance with the inventive principles of the present disclosure.

Referring to FIG. 17A, a flowchart 180a represents one embodiment of torquability detection method 180 (FIG. 12) executable by torquability detector 102 (FIG. 10) on a temporal frame basis as a proximal segment of interventional device 40 (FIG. 10) is being manually or robotically rotated relative to or advanced into an anatomical region.

A stage S182a of flowchart 180a encompasses an initial generation of a torquability metric by torquability detector 102 in response to two (2) frames of shape sensing data 72 (FIG. 10) corresponding to a proximal device node as indicated by proximal device node selection data 43a and a distal device node as indicated by distal device node selection data 43b. More particularly, stage S182a involves a setting by torquability detector 102 of a baseline positon 0° of the proximal device node and the distal device node from a current frame and a determination of a rotation $R_{PSSN}$ of the proximal device node and a rotation $R_{DSSN}$ of the distal device node relative to respective baseline positions whereby the torquability metric is absolute differential between the rotation of the nodes with an absolute value of $\|R_{PSSN} - R_{DSSN}\|$.

A stage S184a of flowchart 180a encompasses a conditional activation of a twisting warning based on an application of a twisting threshold to the torquability metric and/or a conditional activation of a whipping warning based on an application of a whipping threshold to the torquability metric. More particularly, delineating a twisting of the interventional device insusceptible to a whipping of interventional device 40 within the anatomical region, and/or the torquability metric having a non-zero magnitude exceeding a whipping threshold indicative of a delineated twisting of the interventional device susceptible to a whipping of interventional device 40 within the anatomical region.

In practice, either the twisting threshold and/or the whipping threshold may be implemented by torquability detector 102.

If the twisting threshold is exclusively implemented by torquability detector 102, then the twisting threshold may be any magnitude greater than zero whereby a twisting warning will be activated when the torquability metric exceeds the twisting threshold. The twisting warning may be communicated by torquability detector 102 via a color encoding of the displayed reconstructed shape of interventional device 40 within the anatomical region of patient P, a textual display warning, an auditory warning, a visual warning (e.g., an energizing of a hub LED of interventional device 40) and/or haptic feedback (e.g., a vibration of a hub motor of interventional device 40).

In practice, the value of the twisting threshold may be derived from a machine learning or empirically from a plurality of test scenarios.

Similarly, if the whipping threshold is exclusively implemented by torquability detector 102, then the whipping threshold may be any magnitude greater than zero whereby a whipping warning will be activated when the torquability metric exceeds the whipping threshold. The whipping warning may be communicated by torquability detector 102 via a color encoding of the displayed reconstructed shape of interventional device 40 within the anatomical region of patient P, a textual display warning, an auditory warning, a visual warning (e.g., an energizing of a hub LED of interventional device 40) and/or haptic feedback (e.g., a vibration of a hub motor of interventional device 40).

In practice, the value of the whipping threshold may be derived from a machine learning or empirically from a plurality of test scenarios.

Otherwise, if the both the twisting threshold and the whipping threshold are implemented by torquability detector 102, then the twisting threshold will have a magnitude greater than zero and less than a magnitude of the whipping threshold whereby a twisting warning will be activated when the torquability metric exceeds the twisting threshold yet is less than the whipping threshold and whereby a whipping warning will be activated when the torquability metric exceeds the whipping threshold. The twisting warning and the whipping warning may be communicated by torquability detector 102 as previously described in the present disclosure with each warning having a distinctive mode. For example, an activated twisting warning may periodically energize a hub LED while an activated whipping warning may fully energize the hub LED. Also, by example, an activated twisting warning may periodically vibrate a hub motor while an activated whipping warning continually vibrates the hub motor.

An example of a non-activated warning scenario is shown in FIGS. 8A and 9A.

Examples of an activated warning scenario is shown in FIGS. 8B and 9B.

In practice, a twisting warning may be activated at an increasing intensity and an increasing frequency as the torquability metric increasingly exceeds the twisting threshold or as the torquability metric approaches the twisting threshold.

Also in practice, a whipping warning may be activated at an increasing intensity and an increasing frequency as the torquability metric increasingly exceeds the whipping threshold or as the torquability metric approaches the whipping threshold.

Referring back to FIG. 17A, if a warning is not activated during stage S184a as ascertained by torquability detector 102 during a stage S186a of flowchart 180a, then torquability detector 102 returns to stage S182a to process the next frame of proximal device node and distal device node relative to the baseline rotation position.

Otherwise, if a warning is activated during stage S184a as ascertained by torquability detector 102 during stage S186a, then torquability detector 102 proceeds to a stage S188a of flowchart 180a encompassing torquability detector 102 process the next frame to continue the determination of rotation $R_{PSSN}$ of the proximal device node and rotation $R_{DSSN}$ the distal device node relative to respective baseline positions whereby the torquability metric is absolute differential between the rotation of the nodes with an absolute value of $\|R_{PSSN}-R_{DSSN}\|$.

If the torquability detector 102 ascertains during a stage S190a of flowchart 180a that the proximal device node and/or the distal device node have been unrolled to a degree exceeding the twisting threshold or the whipping threshold (whichever is applicable to the activated warning), then torquability detector 102 deactivates the activated warning and returns to stage S182a to process the next frame of proximal device node and distal device node relative to the baseline rotation position Otherwise, torquability detector 102 returns to stage S188a to process the next frame(s) of proximal device node and distal device node until the proximal device node and/or the distal device node have been unrolled to a degree exceeding the twisting threshold or the whipping threshold (whichever is applicable to the activated warning or upon a detection by torquability detector 102 of a whipping of interventional device 40 within the anatomical region.

If the proximal device node and/or the distal device node have been unrolled, then torquability detector 102 returns to state S182a and continues to utilize the current baseline position for generating the torquability metric.

If torquability detector 102 detects a whipping of interventional device 40, then torquability detector 102 returns to state S182a and resets the baseline position for generating the torquability metric.

Examples of whipping scenarios is shown in FIGS. 8C and 9C.

Still referring to FIG. 17A, those skilled in the art of the present disclosure will appreciate that a benefit of flowchart 180a is a systematic conditional activation of a warning of a potential or a likely whipping of interventional device 40.

Figure 17B:
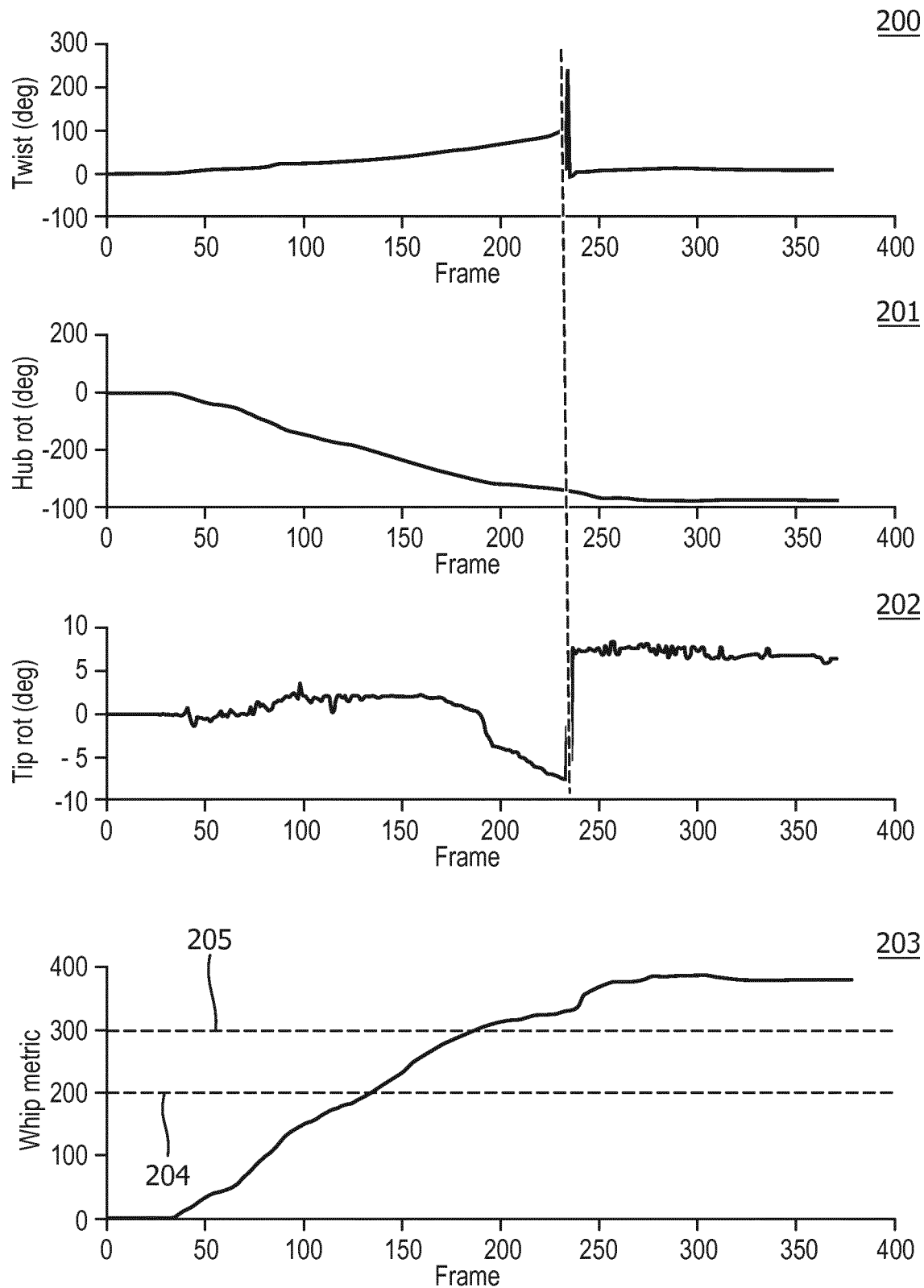
FIGS. 17B and 17C illustrate exemplary graphs of a proximal device node rotation, a distal device node rotation and torquability metrics generated by an execution of the torquability pushability monitoring method of FIG. 17A.
Figure 17C:
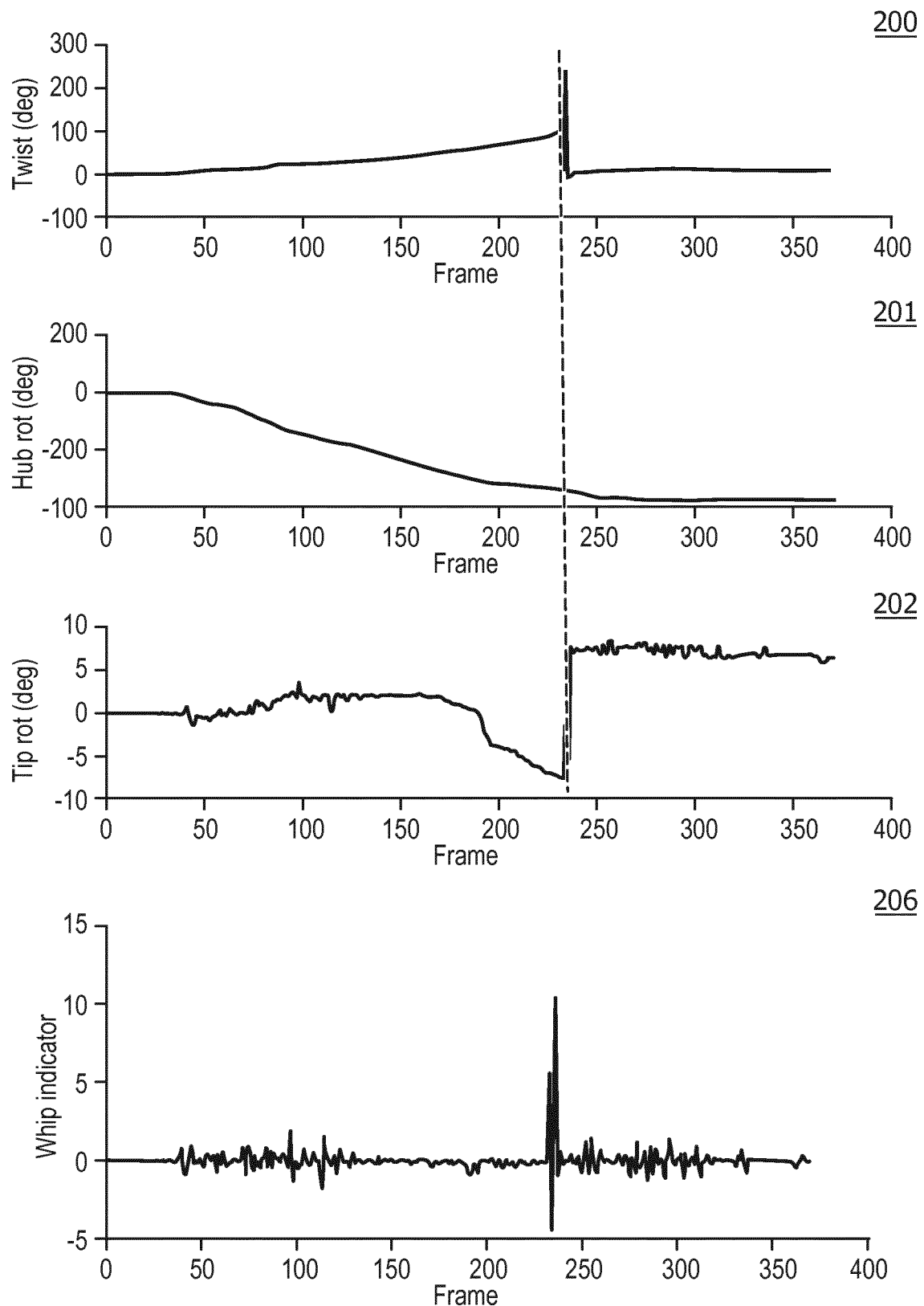

For example, FIGS. 17B and 17C illustrate a graph 200 of an exemplary twisting of interventional device 40, a graph 201 of an exemplary rotation of a hub of interventional device 40 associated with the proximal device node relative to the baseline positon, a graph 202 of an exemplary rotation a distal tip of interventional device 40 associated with the distal device node relative to the baseline positon, a graph 203 of an exemplary torquability metric having a twisting threshold 204 and a whipping threshold 205 (FIG. 17B) and a graph 206 of an exemplary whipping indicator.

For this example, a whipping occurs between frames 200 and 250 whereby torquability detector 102 resets the baseline position.

Referring to FIGS. 1-17, those having ordinary skill in the art will appreciate numerous benefits of the present disclosure including, but not limited to, an improvement over OSS guiding systems, controllers and methods by the inventions of the present disclosure providing a detection of any folding and/or any twisting of an interventional device incorporating an integration of an interventional tool and a OSS sensor as the interventional device is linearly/curvilinearly translated and/or axially/non-axially rotated within an anatomical region.

Furthermore, as one having ordinary skill in the art will appreciate in view of the teachings provided herein, features, elements, components, etc. described in the present disclosure/specification and/or depicted in the Figures may be implemented in various combinations of electronic components/circuitry, hardware, executable software and executable firmware and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the inventive principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present disclosure can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present disclosure and disclosure.

Having described preferred and exemplary embodiments of novel and inventive OSS guiding and monitoring systems, controllers and methods, (which embodiments are intended to be illustrative and not limiting), it is noted that modifications and variations can be made by persons having ordinary skill in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. An optical shape sensing (OSS) guiding and monitoring system, comprising:
    an interventional device including an integration of a OSS sensor and at least one interventional tool,
        wherein the OSS sensor is structurally configured to generate shape sensing data informative of a shape of the OSS sensor as the interventional device is navigated within an anatomical region; and
    an OSS guiding and monitoring device including
        an OSS guiding controller structurally configured to control a reconstruction of a shape of the interventional device within the anatomical region responsive to a generation of the shape sensing data by the OSS sensor; and
        an OSS monitoring controller structurally configured to designate a proximal OSS node and distal OSS node of the OSS sensor, and to control a monitoring of a degree of folding and a degree of twisting of the interventional device within the anatomical region between the proximal OSS node and the distal OSS node including the OSS monitoring controller generating at least one of a pushability metric and a torquability metric responsive to a generation of the shape sensing data by the OSS sensor between a proximal device node and a distal device node, wherein: the pushability metric quantifies an estimated degree of folding of the interventional device between a proximal device node and a distal device node of the interventional device; and the torquability metric quantifies an estimated degree of twisting of the interventional device between a proximal device node and a distal device node of the interventional device.

2. The OSS guiding and monitoring system of claim 1, wherein the OSS monitoring controller controls the monitoring of the at least one of the degree of folding and the degree of twisting of the interventional device within the anatomical region relative to the proximal OSS node and the distal OSS node.

3. The OSS guiding system of claim 1, wherein the OSS monitoring controller is further structurally configured to apply at least one of a folding threshold and a buckling threshold to the pushability metric;
    wherein the folding threshold delineates a folding of the interventional device capable of being further advanced within the anatomical region; and
    wherein the buckling threshold delineates a folding of the interventional device incapable of being further advanced within the anatomical region.

4. The OSS guiding system of claim 1,
wherein the OSS monitoring controller is further structurally configured to apply at least one of a twisting threshold and a whipping threshold to the torquability metric;
wherein the twisting threshold delineates a twisting of the interventional device insusceptible of a whipping of the interventional device within the anatomical region; and
wherein the whipping threshold delineates a twisting of the interventional device susceptible of a whipping of the interventional device within the anatomical region.

5. The OSS guiding system of claim 1,
wherein the OSS monitoring controller is further structurally configured to control a conditional warning of at least one of a folding and a twisting of the interventional device within the anatomical region; and
wherein the conditional warning includes at least one of:
  a textual display warning associated with a display of the reconstruction of the shape of the interventional device within the anatomical region,
  an auditory display warning associated with the display of the reconstruction of the shape of the interventional device within the anatomical region,
  a visual display warning associated with the display of the reconstruction of the shape of the interventional device within the anatomical region,
  a visual device warning generated by the interventional device, and
  a haptic warning generated by the interventional device.

6. The OSS guiding system of claim 1,
wherein, as indicated by the shape sensing data, the OSS monitoring controller is further structurally configured to derive the pushability metric from an advancement of a proximal device node of the interventional device extraneous to the anatomical region relative to any translation of a distal device node of the interventional device.

7. The OSS guiding system of claim 1,
wherein, as indicated by the shape sensing data, the OSS monitoring controller is further structurally configured to derive the torquability metric from a curvature of the interventional device between the proximal device node and the distal device node of the interventional device as the interventional device is navigated within the anatomical region.

8. The OSS guiding system of claim 1,
wherein, as indicated by the shape sensing data, the OSS monitoring controller is further structurally configured to derive the pushability metric from forces applied to the interventional device as the interventional device is navigated within the anatomical region.

9. The OSS guiding system of claim 1,
wherein, as indicated by the shape sensing data, the OSS monitoring controller is further structurally configured to derive the torquability metric from any rotation of the proximal device node of the interventional device extraneous to the anatomical region relative to any rotation of the distal device node of the interventional device within the anatomical region.

10. The OSS guiding system of claim 1,
wherein, as indicated by the shape sensing data, the OSS monitoring controller is further structurally configured to derive the torquability metric from any rotation of the distal device node of the interventional device as the interventional device is navigated within the anatomical region.

* * * * *